United States Patent [19]

Vandenberk et al.

[11] 4,126,688

[45] Nov. 21, 1978

[54] ANTIEMETIC 1-(BENZOTRIAZOLYL-ALKYL)-PIPERIDINE DERIVATIVES

[75] Inventors: Jan Vandenberk, Beerse; Ludo E. J. Kennis, Vosselaar; Marcel J. M. C. Van der Aa, Vosselaar; Albert H. M. Th. Van Heertum, Vosselaar, all of Belgium

[73] Assignee: Janssen Pharmaceutica N.V., Beerse, Belgium

[21] Appl. No.: 817,397

[22] Filed: Jul. 20, 1977

Related U.S. Application Data

[60] Division of Ser. No. 687,139, May 17, 1967, Pat. No. 4,066,772, which is a continuation-in-part of Ser. No. 597,793, Jul. 21, 1975, abandoned.

[51] Int. Cl.$^2$ .............. A61K 31/445; C07D 401/06; C07D 401/14
[52] U.S. Cl. .................. 424/267; 424/263; 546/16; 546/199; 546/271
[58] Field of Search ............... 260/295 K, 294.8 C, 260/293.6, 293.59; 424/263, 267

[56] References Cited

U.S. PATENT DOCUMENTS 3,634,441  1/1972  Welstead et al. ............ 260/293.6

Primary Examiner—Henry R. Jiles
Assistant Examiner—Richard A. Schwartz
Attorney, Agent, or Firm—Salvatore R. Conte

[57] ABSTRACT

Compounds of the class of 1-(benzazolylalkyl)piperidine derivatives useful as antiemetic agents.

10 Claims, No Drawings

ANTIEMETIC 1-(BENZOTRIAZOLYL-ALKYL)-PIPERIDINE DERIVATIVES

CROSS-REFERENCE TO RELATED APPLICATIONS

This is a division of application Ser. No. 687,139 filed May 17, 1976 now U.S. Pat. No. 4,066,772, filed Jan. 3, 1978 which in turn is a continuation-in-part of Ser. No. 597,793 filed July 21, 1975, now abandoned.

BACKGROUND OF THE INVENTION

In the prior art there may be found a number of benzazolylalkyl and indolylalkyl substituted piperidine derivatives and a number of aminoalkyl substituted benzazoles some of them having pharmacological, e.g. antidepressant, anticonvulsant, antihistaminic or antispasmogenic activities.

Among other points of difference, the subject compounds of this invention differ from such known compounds by the nature of respectively the benzazole and/or substituted piperidine moiety within their structure.

A number of the aforementioned prior art compounds may be found in the following references:
Int. Pharmacopsychiat. 1968 (1), p. 214;
C.A., 64, 2093 b (1966);
C.A., 72, 111466 (1970);
C.A., 81, 120632 b (1974);
Fr. Pat. No. 2,042,321 (Derw. Fr. Week S16, Pharm. p. 12); and
Belg. Pat. No. 753,472.

DESCRIPTION OF THE PREFERRED EMBODIMENTS

The novel 1-(benzazolylalkyl)piperidine derivatives of this invention may structurally be represented by the following formula:

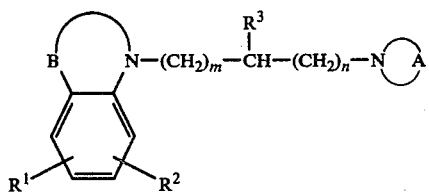

and the pharmaceutically acceptable acid addition salts thereof, wherein:
$R^1$ and $R^2$ are each independently selected from the group consisting of hydrogen, halo, lower alkyl and trifluoromethyl;
B is a member selected from the group consisting of the bivalent radicals

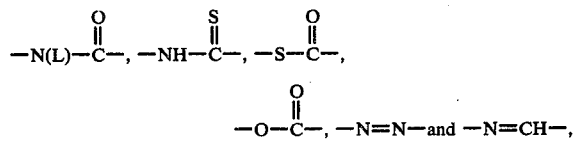

said L being a member selected from the group consisting of hydrogen, lower alkyl, lower alkylcarbonyl and lower alkenyl, and said bivalent radicals being attached to the benzene nucleus with their heteroatom;

$R^3$ is a member selected from the group consisting of hydrogen and methyl;
m and n are each an integer of from 1 to 2 inclusive; and the radical

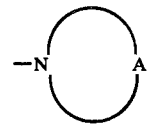

is a member selected from the group consisting of:
a. a radical having the formula

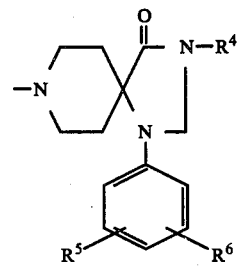

wherein $R^4$ is a member selected from the group consisting of hydrogen and lower alkyl; and $R^5$ and $R^6$ are each independently selected from the group consisting of hydrogen, halo lower alkyl and trifluoromethyl;

b. a radical having the formula:

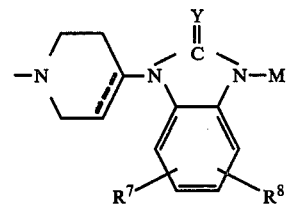

wherein $R^7$ and $R^8$ are each independently selected from the group consisting of hydrogen, halo, lower alkyl and trifluoromethyl; Y is a member selected from the group consisting of O and S; M is a member selected from the group consisting of hydrogen, lower alkyl and lower alkylcarbonyl; and the dotted line indicates that the double bond between the 3 and 4 carbon atoms of the piperidine nucleus is optional, provided that when said Y is S then there is a single bond between said 3 and 4 carbon atoms of the piperidine nucleus and then said M is hydrogen:

c. a radical having the formula:

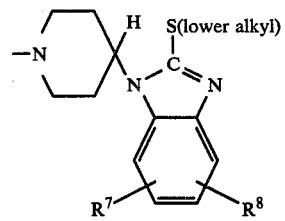

wherein $R^7$ and $R^8$ are each independently selected from the group consisting of hydrogen, halo, lower alkyl and trifluoromethyl; and
d. a radical having the formula:

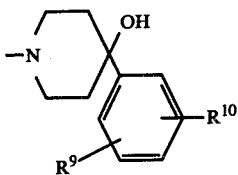

wherein $R^9$ is selected from the group consisting of hydrogen, halo, lower alkyl and trifluoromethyl, and $R^{10}$ is selected from the group consisting of hydrogen and halo.

As used herein "lower alkyl" may be straight or branch chained and have from 1 to 5 carbon atoms, such as, for example, methyl, ethyl, propyl, 1-methylethyl, butyl, pentyl and the like; "lower alkenyl" may be a straight or branch chained alkenyl radical having from 2 to 5 carbon atoms, such as, for example, 1-methylethenyl, 2-propenyl, 2-butenyl, 3-butenyl, 2-pentenyl and the like; and the term "halo" is generic to halogens of atomic weight less than 127, i.e., fluoro, chloro, bromo and iodo.

Compounds of formula (I) which may be represented by the formula:

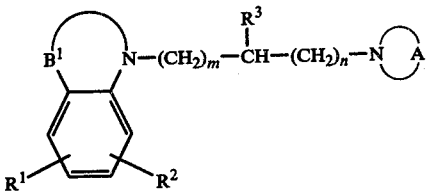
(I-a)

wherein $R^1$, $R^2$, $R^3$, $m$, $n$ and

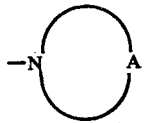

are as previously defined and $B^1$ is as defined for B, but other than —NH—C(S)—, are conveniently prepared by reacting an appropriate reactive ester of formula (II) wherein X is an appropriate reactive ester function derived from the corresponding alcohol, such as, for example, halo, methanesulfonyl, 4-methylbenzenesulfonyl and the like, with an appropriate piperidine derivative of formula (III) wherein the

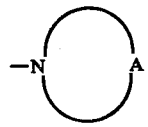

group is as defined hereinabove.

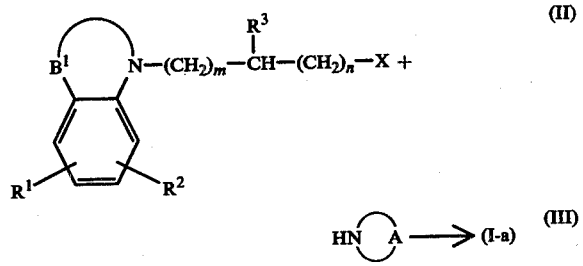

The foregoing condensation reaction is preferably carried out in an appropriate organic solvent, such as, for example, a lower alkanol, e.g. methanol, ethanol, propanol, butanol and the like alcohols; an aromatic hydrocarbon, e.g. benzene, methylbenzene, dimethylbenzene, and the like; a ketone, e.g. 4-methyl-2-pentanone; an ether, e.g. 1,4-dioxane, 1,1'-oxybisethane and the like; N,N-dimethylformamide; nitrobenzene; and the like. The addition of an appropriate base, such as, for example, an alkali metal or earth alkali metal carbonate or hydrogen carbonate, may be utilized to pick up the acid that is liberated during the course of the reaction. A small amount of an appropriate metal iodide, e.g. sodium or potassium iodide, may be added as a reaction promotor, especially when the reactive ester of formula (II) is a chloride. Somewhat elevated temperatures are appropriate to enhance the rate of the reaction and preferably the reaction is carried out at the reflux temperature of the reaction mixture. In this and following procedures, the reaction products are separated from the medium and, if necessary, further purified by the application of methodologies known in the art.

Compounds within the scope of formula (I) which may be represented by the formula:

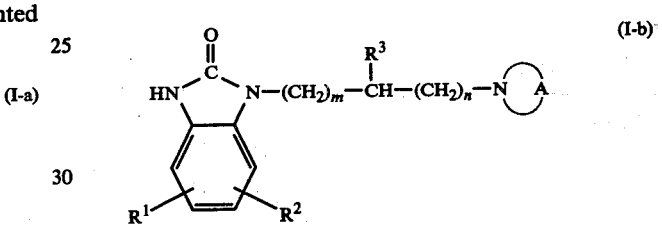
(I-b)

wherein $R^1$, $R^2$, $m$, $n$, $R^3$ and

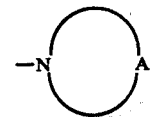

are as previously defined may also be prepared starting from the corresponding compounds of formula (IV)

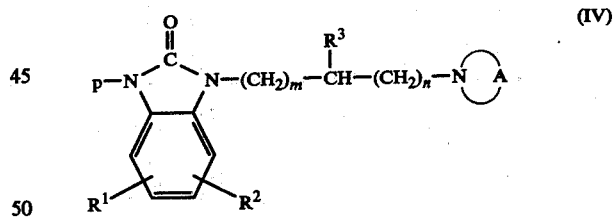
(IV)

wherein P is an appropriate protecting group, by the removal of said protecting group according to conventional procedures as known in the art. Examples of such protecting groups are, among others, lower alkyloxycarbonyl, 4-methylbenzenesulfonyl, methanesulfonyl and, preferably a substituted ethenyl group of the formula:

$$R^{12}-CH=C-\underset{R^{11}}{|}$$

wherein $R^{11}$ and $R^{12}$ may represent different groups but wherein $R^{11}$ is preferably lower alkyl and $R^{12}$ is preferably hydrogen, lower alkyl or phenyl.

When the protecting group is lower alkyloxycarbonyl, 4-methylbenzenesulfonyl or methanesulfonyl, it may easily be removed by alkaline hydrolysis, and when the protecting group is a substituted ethenyl group it is conveniently eliminated by subjecting the appropriate intermediate (IV) to acid hydrolysis. In carrying out said acid hydrolysis to remove the substituted ethenyl group from (IV) a wide variety of protonic acids may be employed including mineral acids, such as, for example, hydrochloric, hydrobromic, sulfuric, nitric and phosphoric acid, and organic acids such as, for example, acetic, propanoic and the like acids. Further the reaction may be carried out in reaction-inert organic solvents as commonly employed in such a type of hydrolytic reactions, e.g., methanol, ethanol, 2-propanone and the like.

Compounds within the scope of formula (I) which may be represented by the formula:

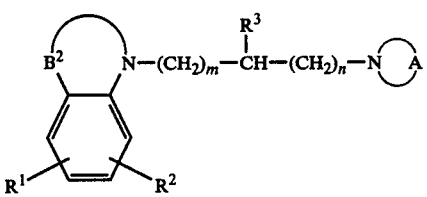

(I-c)

wherein $R^1$, $R^2$, $m$, $n$, $R^3$ and $$-N\underset{\smile}{\overset{\frown}{}}A$$

are as previously defined and $B^2$ is selected from the group consisting of —NH—C(O)—, —NH—C(S)— and —N=CH—, may still be prepared by subjecting an appropriate benzenediamine of formula (V) to ring closure with an appropriate cyclizing agent, the nature of which depends on the nature of $B^2$ in the desired product.

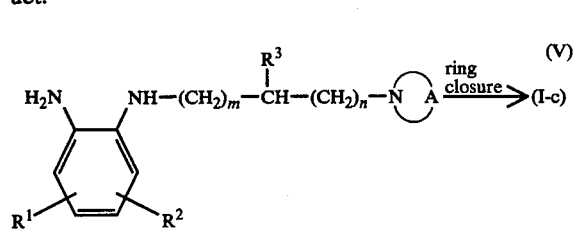

(V)

The foregoing cyclization reaction may be performed following art-known procedures of preparing 1H-benzimidazoles, 1,3-dihydro-2H-benzimidazol-2-ones, and 1,3-dihydro-2H-benzimidazol-2-thiones starting from 1,2-benzenediamines. Suitable cyclizing agents which may advantageously be employed to prepare compounds (I-c) wherein $B^2$ stands for —NH—C(O)—, include, for example, urea, carbonyl dichloride and alkali metal isocyanates, and the cyclisation reaction may be carried out following methodolgies generally known in the art. For example, when urea is used as the cyclizing agent the desired compounds are easily obtained by stirring and heating the reactants together in the absence of any solvent.

When $B^2$ in the desired compounds (I-c) stands for —NH—C(S)—, there may be used cyclizing agents such as, for example, carbon disulfide, thiourea, carbonothioic dichloride, ammonium thiocyanate and the like, and when $B^2$ stands for —N=CH—, there may be used formic acid or an appropriate tri(alkyloxy)methane as a cyclizing agent.

In a manner similar to that described hereabove there may be prepared compounds of the formula:

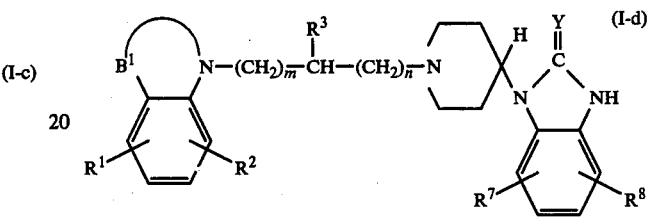

(I-d)

wherein $R^1$, $R^2$, $R^3$, $R^7$, $R^8$, $m$, $n$, $B^1$ and Y are as previously defined, by cyclizing an appropriate benzenediamine of formula (VI) with an appropriate cyclizing agent.

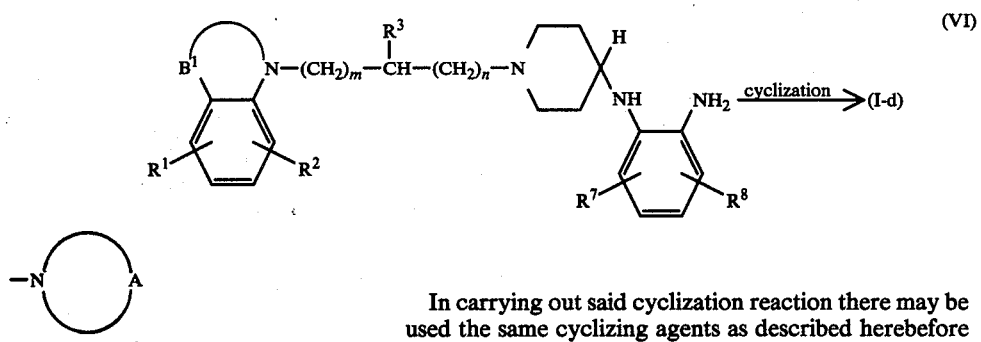

(VI)

In carrying out said cyclization reaction there may be used the same cyclizing agents as described herebefore for the preparation of compounds (I-c) starting from (V), more specifically for the preparation of compounds (I-c) wherein $B^2$ stands for respectively —NH—C(O)— and —NH—C(S)—.

Still in a similar manner there may be prepared compounds of the formula:

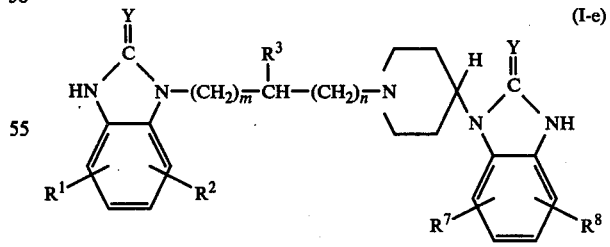

(I-e)

wherein $R^1$, $R^2$, $R^3$, $R^7$, $R^8$, $m$ and $n$ are as previously defined and the two Y groups are both O or both S, starting from the corresponding intermediates of formula (VII) by cyclizing both benzenediamine groups in said (VII) in one reaction step with an appropriate cyclizing agent as described hereinabove for the preparation of respectively 1,3-dihydro-1H-benzimidazol-2-ones and 1,3-dihydro-1H-benzimidazol-2-thiones.

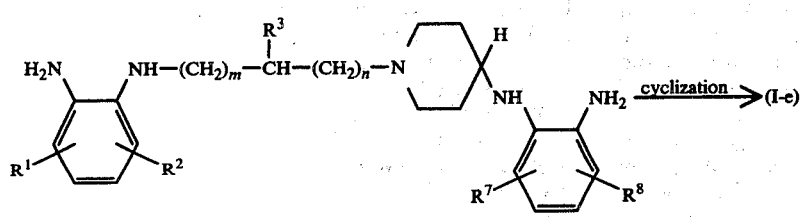

Compounds having the formula:

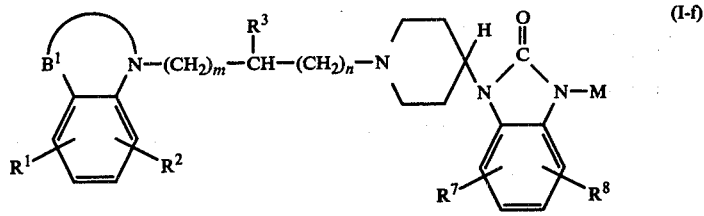

wherein $R^1$, $R^2$, $R^3$, $R^7$, $R^8$, $m$, $n$ and $B^1$ are as previously defined and $M^1$ is lower alkyl or lower alkylcarbonyl may still be prepared by respectively N-alkylating or N-acylating the corresponding unsubstituted compound with an appropriate alkylating, respectively acylating agent following art-known methodologies. The N-alkylation may e.g. be carried out by the reaction of the unsubstituted compound with an appropriate reactive ester derived from an appropriate lower alkanol, e.g., a halo-lower alkane, or a lower alkyl methanesulfonate or 4-methylbenzenesulfonate under similar conditions as described hereinabove for the preparation of the compound (I-a) starting from (II) and (III). The acylation may be carried out by reacting the unsubstituted compound with an anhydride or acylhalide derived from the appropriate lower alkylcarboxylic acid following standard N-acylating procedures as known in the art.

When $B^1$ in the compounds (I-f) stands for —NH—C(O)—, it is appropriate to start from an appropriate compound of formula:

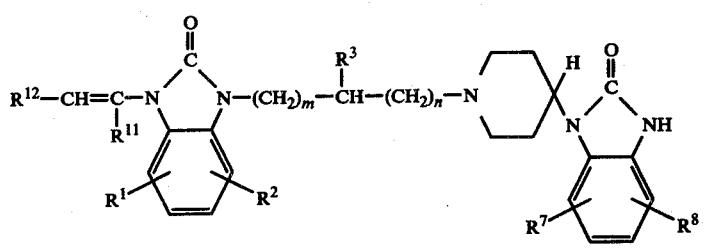

which is then N-alkylated, respectively N-acylated as described hereabove, whereafter the substituted ethenyl protecting group is eliminated by acid hydrolysis.

Those compounds of formula (I-f) wherein $B^1$ stands for —N(L)—C(O)—, said L being a lower alkyl or lower alkylcarbonyl radical identical with $M^1$, may still be prepared starting from an appropriate compound of formula (I-e) wherein Y stands for O, by alkylating, respectively acylating both 1H-benzimidazole groups thereof in one reaction step.

Compounds having the formula:

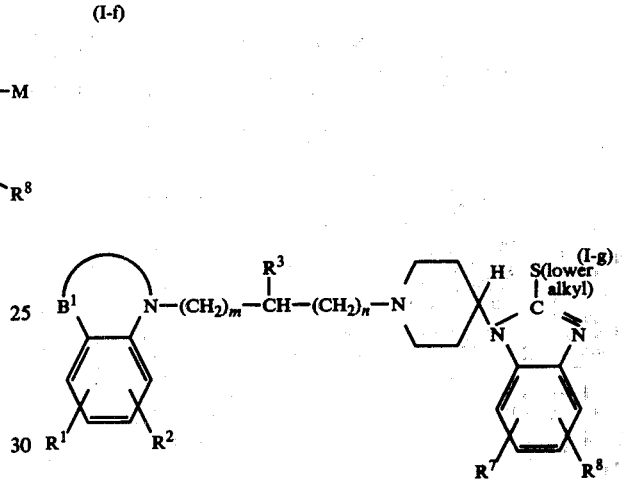

may still be prepared starting from a corresponding compound of formula (I-d) wherein Y stands for S, (I-d-1), by S-alkylation of the latter according to standard S-alkylating procedures, e.g., by the reaction of (I-d-1) with an appropriate halo-lower alkane or with an appropriate di-(lower alkyl)sulfate.

The starting materials used in the foregoing preparations may be obtained following the procedures indicated hereafter.

Reactive esters of formula (II) which may be represented by the formula:

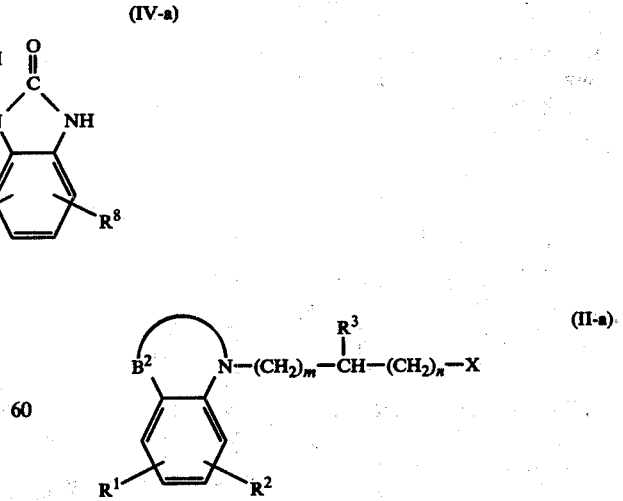

wherein $R^1$, $R^2$, $R^3$, $m$, $n$, $B^2$ and X are as previously defined may be prepared as follows:

An appropriately substituted 2-chloronitrobenzene of formula (VIII) is reacted with an appropriate aminoalkanol (IX) by refluxing the reactants together in an appropriate reaction-inert organic solvent such as, for example, a lower alkanol, e.g., ethanol, 2-propanol, butanol and the like, whereupon a [(2-nitrophenyl)amino]alkanol of formula (X) is obtained, which in turn is subjected to a nitro-to-amine reduction, e.g. by catalytic hydrogenation using Raney-nickel catalyst. The thus obtained [(2-aminophenyl)amino]alkanol of formula (XI) is then reacted with an appropriate cyclizing agent as described hereinbefore for the preparation of the compounds (I-c) starting from (V), and the thus obtained alcohol (XII) is subsequently converted into the desired reactive ester (II-a) by the application of methodologies known in the art.

Halides are conveniently prepared by the reaction of (XII) with an appropriate halogenating agent such as, for example, sulfinyl chloride, sulfuryl chloride, phosphor pentachloride, phosphor pentabromide, phosphoryl chloride and the like. When the reactive ester is an iodide, it is preferably derived from the corresponding chloride or bromide by the replacement of that halogen with iodine. Other reactive esters such as methanesulfonates and 4-methylbenzenesulfonates are obtained by the reaction of the alcohol with an appropriate sulfonyl halide such as, for example, methanesulfonyl chloride and 4-methylbenzenesulfonyl chloride respectively.

The foregoing reactions are more clearly illustrated in the following schematic representation.

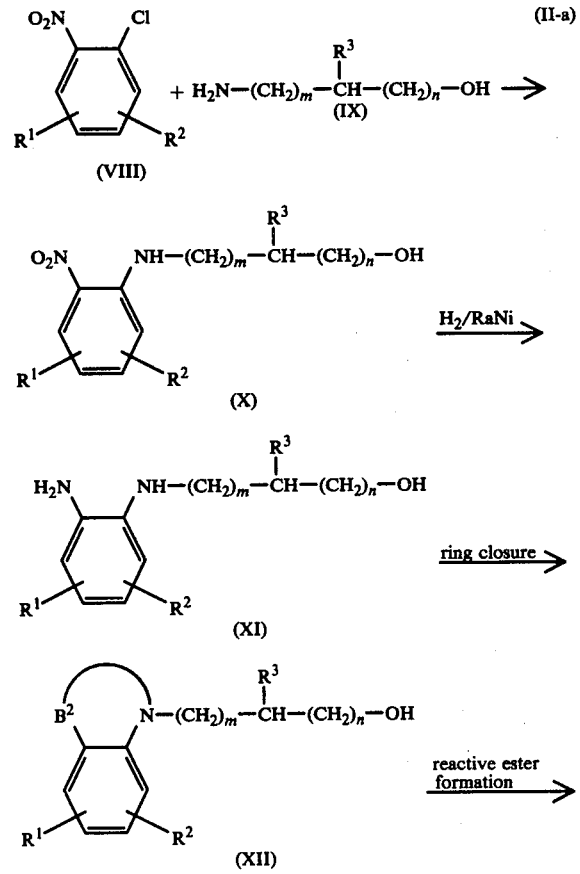

Intermediates of formula (II) which may be represented by the formula

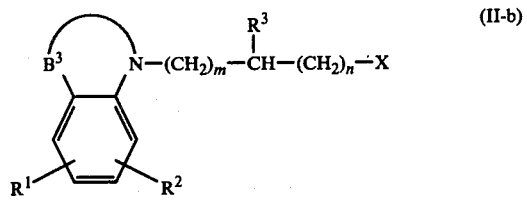

wherein $R^1$, $R^2$, $R^3$, $m$, $n$ and $X$ are as previously defined and $B^3$ is selected from the group consisting of —S—C(O)—, —O—C(O)—, —N=N—, —N=CH—, and —N($L^1$)—C(O)— wherein $L^1$ is lower alkyl, lower alkenyl, or lower alkylcarbonyl, may also conveniently be prepared by the introduction of the reactive ester side chain into a starting material of the formula

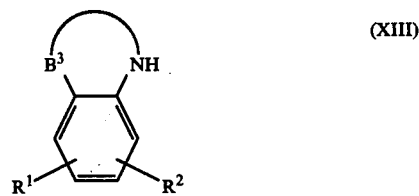

following procedures known in the art. For example, one may first introduce a hydroxyalkyl chain by N-alkylating (XIII) with an appropriate haloalkanol of formula (XIV) following common N-alkylating procedures to obtain an alcohol of formula (XV), the hydroxyl group of which is subsequently converted into a reactive ester group according to conventional procedures as previously described.

In place of the haloalkanol (XIV) there may also be used a tetrahydro-2H-pyran-2-yl ether derivative thereof, in which case the corresponding ether derivative of (XV) is obtained, the ether function of which is split open by acid hydrolysis, e.g., by stirring and heating the ether compound in diluted hydrochloric acid.

When the reactive ester (II-b) is a halide, (II-b-1), it may alternatively be prepared by the reaction of (XIII) with an equivalent of an appropriate dihaloalkane (XVI), in the presence of an appropriate strong base such as, for example, sodium methanolate, or following a Mackosza procedure using aqueous alkali and a quaternary ammonium catalyst, e.g., N,N,N-triethylbenzenemethanaminium chloride, yielding the desired intermediate (II-b-1).

The foregoing procedure may be illustrated as follows.

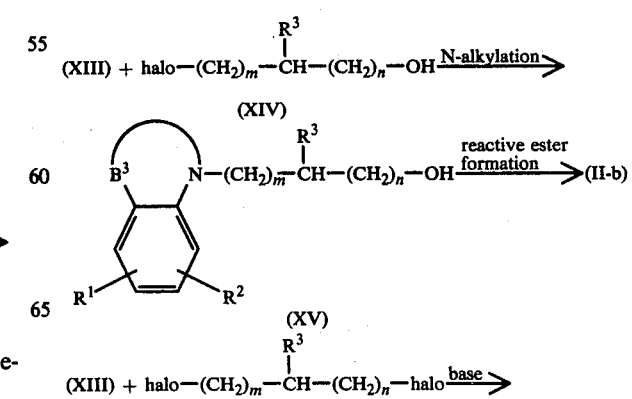

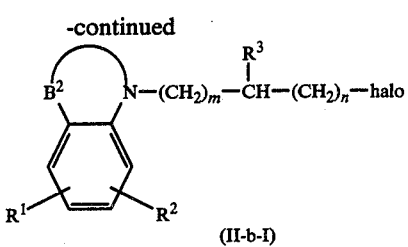

(II-b-1)

Intermediates of the formula:

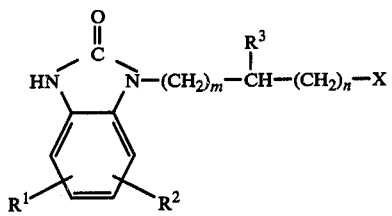

(II-c)

wherein $R^1$, $R^2$, $R^3$, $m$, $n$ and X are as previously defined may still be prepared by introducing the reactive ester side chain into a starting material of formula (XVII)

wherein P is an appropriate protecting group as previously defined, and thereafter eliminating the protecting group of the thus obtained (XIX) according to art-known procedures as described hereinabove. The introduction of the reactive ester side chain may be performed following similar procedures to those described hereabove for the introduction of said chain into starting materials of formula (XIII). More particularly there may be first introduced a hydroxyalkyl chain, whereafter the hydroxyl group of the thus obtained intermediate (XVIII) is converted into a reactive ester group to obtain (XIX), or, when the reactive ester is a halide, (XIX-a) said halide may be obtained directly by the reaction of (XVII) with an appropriate dihaloalkane. When the protecting P is one subject to alkaline hydrolysis, e.g., a lower alkyloxycarbonyl, methanesulfonyl or 4-methylbenzenesulfonyl group, the N-alkylation reaction to introduce respectively the hydroxyalkyl or haloalkyl chain should be carried out under non-hydrolytic conditions, using for example an appropriate metal base such as, for example, sodium hydride or sodium methanolate in an appropriate aprotic organic solvent such as, for example, N,N-dimethylformamide, N,N-dimethylacetamide or hexamethylphosphoric triamide.

The foregoing reactions are more clearly illustrated in the following schematic representation.

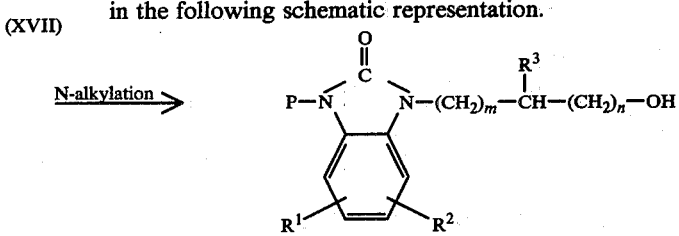

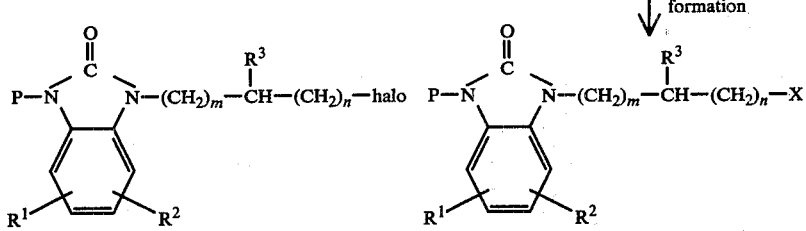

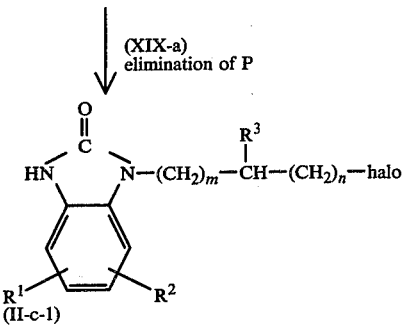

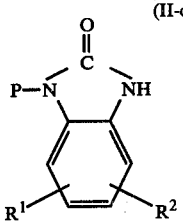

Intermediates having the formula

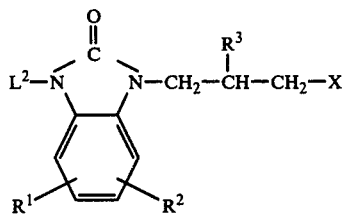

wherein $R^1$, $R^2$, $R^3$ and X are as previously defined and $L_2$ is lower alkyl or lower alkenyl, said lower alkenyl having its unsaturation at the $\beta$, $\gamma$ or $\delta$-position, may still be prepared as follows.

An appropriate intermediate of formula (II-c), wherein m and n are each 1, (II-c-2), is treated with sodium metal in absolute ethanol whereby a cyclic ether of formula (XX) is formed. The latter is subsequently reacted with an appropriate reactive ester $L^2X$, (XXI), wherein $L_2$ and X are as previously defined, e.g., by refluxing the reactants together in an appropriate organic solvent such as, for example, 2-propanone, whereby the desired intermediate (II-d) is obtained.

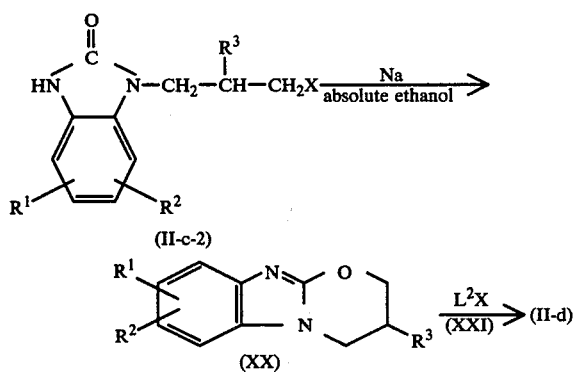

The compounds of formula (IV), used as intermediates in the preparation of the compounds (I-b), may generally be obtained by a condensation reaction of an intermediate of formula (XIX) with an appropriate intermediate of formula (III) under similar conditions to those described hereinabove for the preparation of the compounds (I-a) starting from (II) and (III).

$$(XIX) + (III) \rightarrow (IV)$$

Those intermediates of formula (IV) wherein

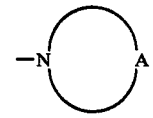

has the formula

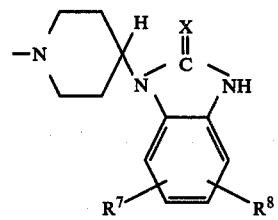

and which are indicated as (IV-b) may still be prepared by the condensation of an appropriate reactive ester of formula (XIX) with an appropriate N-(2-nitrophenyl)-4-piperidinamine of formula (XXII), followed by the reduction of the nitro group of the thus obtained (XXIII) according to standard nitro-to-amine reduction procedures, e.g., by the reaction of the nitro compound with nascent hydrogen or by catalytic hydrogenation in the presence of an appropriate catalyst such as, for example, Raney-nickel, and cyclization of the resulting benzenediamine (XXIV) with an appropriate cyclizing agent as described hereinabove.

The foregoing reactions are illustrated in the following schematic representation.

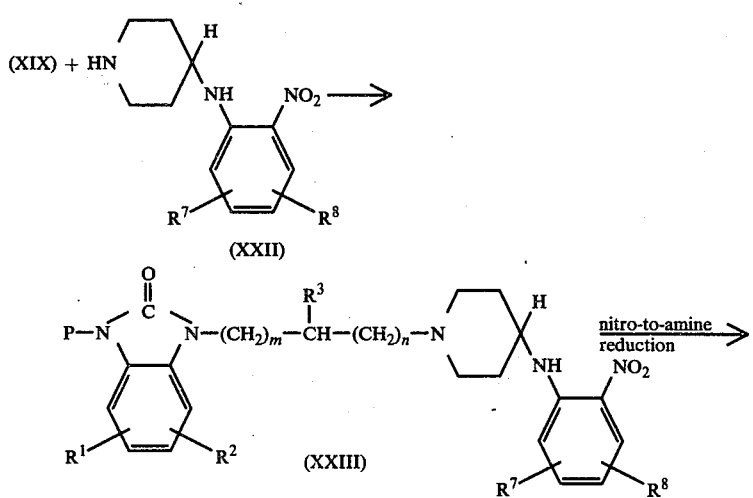

-continued

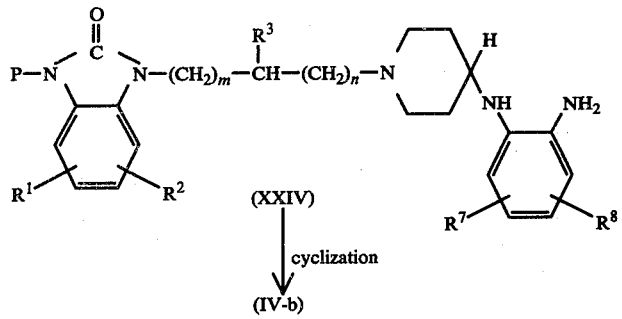

The starting materials of formula (XXII) herein may be prepared following the procedures outlined in U.S. Pat. No. 3,910,930.

The intermediates of formula (V) are obtained by the condensation of an appropriate reactive ester of formula (XXV) with an appropriate piperidine derivative of formula (III), followed by the reduction of the nitro group of the thus obtained intermediate (XXVI) to an amino group according to standard nitro-to-amine reduction procedures.

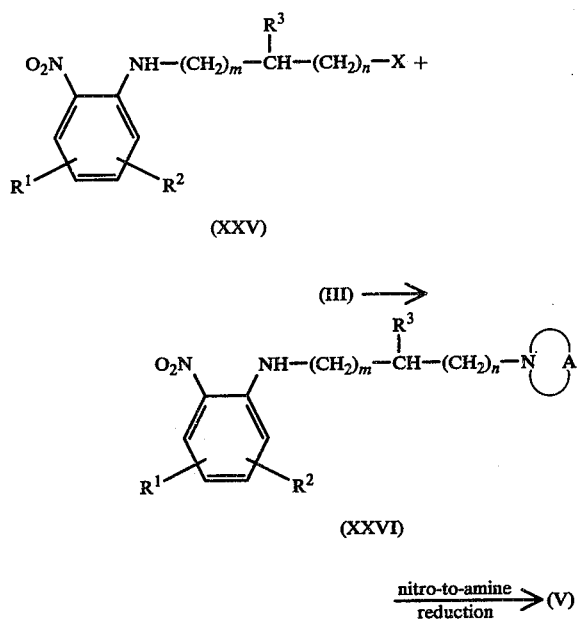

The reactive esters of formula (XXV), used as starting materials herein are easily prepared starting from an alcohol of formula (X) by the conversion of the hydroxyl function thereof into a reactive ester group following standard procedures as previously described herein.

The intermediates of formula (VI) may generally be prepared by the condensation of an appropriate reactive ester of formula (II) with an appropriate N-(2-nitrophenyl)-4-piperidinamine of formula (XXII) and subsequent reduction of the nitro group of the thus obtained (XXVII) to an amine group following standard nitro-to-amine reduction procedures as previously described.

It is to be noted that when the nitro-to-amine reduction is accomplished by catalytic hydrogenation using palladium-on-charcoal catalyst there may occur dehalogenation in compounds wherein aromatic halogen substituents are present.

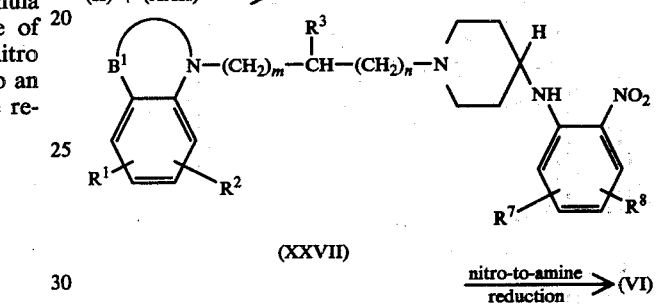

The intermediates of formula (VII) may similarly be prepared by the condensation of a reactive ester of formula (XXV) with a piperidine derivative of formula (XXII) followed by the reduction of both nitro groups in the thus obtained (XXVIII) according to standard procedures as previously indicated.

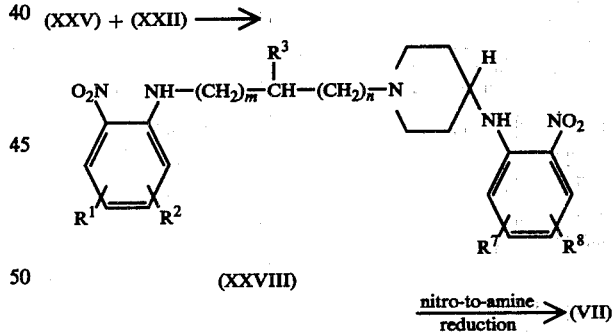

Starting materials of formula (III), represented by the formulas:

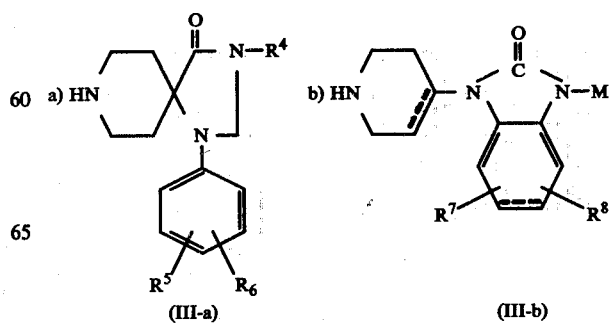

-continued

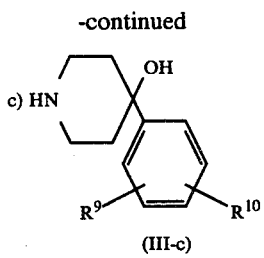
(III-c)

and methods of preparing the same may respectively be found in the following references:

a. U.S. Pat. No. 3,238,216;
b. U.S. Pat. No. 3,161,645; Belg. Pat. No. 830,403;
c. U.S. Pat. No. 3,518,276; and U.S. Pat. No. 3,575,990.

Starting materials of formula (III) which are represented by the formulas:

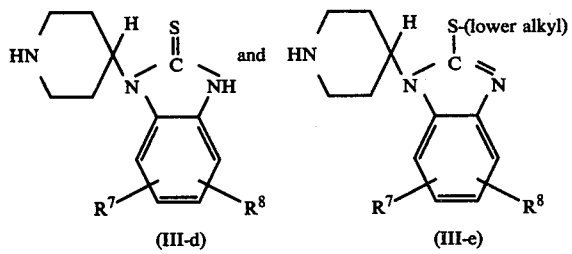

may generally be prepared starting from an appropriate N-(2-aminophenyl)-4-piperidinamine of formula:

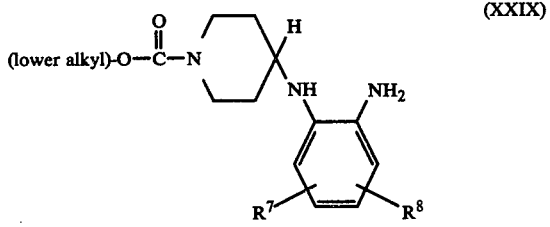

The starting materials (III-d) are conveniently prepared by the cyclization of (XXIX) with an appropriate cyclizing agent e.g., carbon disulfide and subsequent removal of the lower alkyloxycarbonyl group of the thus obtained (XXX) by alkaline hydrolysis.

The starting materials (III-e) can be prepared by S-alkylating (XXX) as described hereinabove followed by elimination of the lower alkyloxycarbonyl group of the resulting (XXXI).

The N-(2-aminophenyl)-4-piperidinamines of formula (XXIX), a number of which are known compounds, may be prepared following the procedures outlined in U.S. Pat. No. 3,910,930 and Belg. Pat. No. 830,403.

The foregoing procedures are illustrated in the following schematic representation.

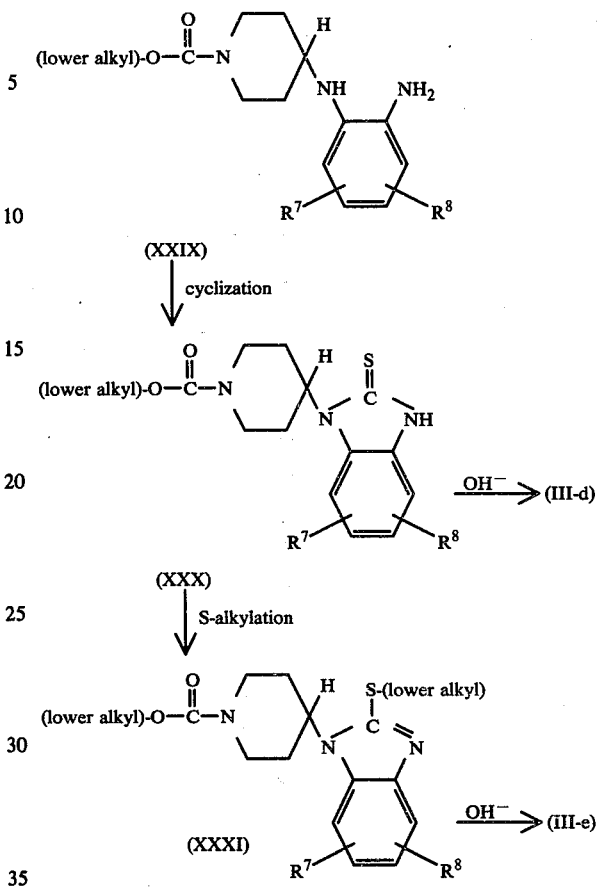

The ultimate starting materials in all of the foregoing preparations are generally known or their preparation may be performed following art-known procedures of preparing similar compounds.

For example, the preferred starting materials of formula (XVII) wherein P is an appropriately substituted ethenyl group, (XVII-a), an important number of which are known compounds, may be prepared following the procedures outlined in J. Chem. Soc., 1960, p. 308 and p. 314.

More particularly such compounds are conveniently prepared by the reaction of an appropriate ester of the formula (XXXII) wherein $R^{11}$ and $R^{12}$ have the previously indicated meaning, with an appropriate benzenediamine of formula (XXXIII). Said reaction is preferably carried out by stirring and refluxing the reactants together in an appropriate reaction-inert organic solvent with azeotropic water removal. Suitable reaction-inert organic solvents for this purpose include, for example, aromatic hydrocarbons such as benzene, methylbenzene, dimethylbenzene and the like.

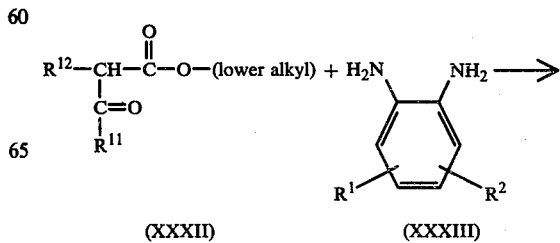

-continued

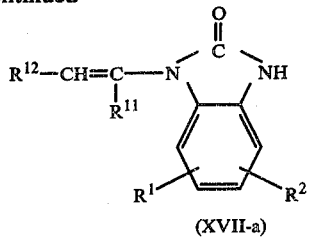

(XVII-a)

The intermediates of formulas (V), (VI) and (VII) are deemed to be novel and, as useful intermediates in the preparation of the desired compounds of formula (I), they constitute an additional feature of this invention.

The compounds of this invention may be converted to their therapeutically useful acid addition salts by treatment with an appropriate acid, such as, for example, an inorganic acid, such as hydrohalic acid, e.g., hydrochloric, hydrobromic, and the like; and sulfuric acid, nitric acid, phosphoric acid and the like; or an organic acid, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) and the therapeutically active acid addition salts thereof have been found to possess strong antiemetic activity as is evidenced by their ability to block apomorphine-induced vomiting in dogs. The method used is described previously by P. A. J. Janssen and C. J. E. Niemegeers in: Arzneim.-Forsch. (Drug Res.), 9, 765–767 (1959).

The compounds listed below were administered subcutaneously to beagle dogs at different doses and the animals were challenged 1 hour thereafter with a standard dose of 0.31 mg/kg (subcutaneous) of apomorphine.

The tables below give the $ED_{50}$ values of a number of the compounds under consideration. As used herein the $ED_{50}$ value represents the dose which protects 50% of the animals from emesis.

It is understood that the compounds shown in the tables are not listed for the purpose of limiting the invention thereto, but only to exemplify the outstanding antiemetic properties of all the compounds within the scope of the formula (I).

TABLE I

| L | $R^1$ | $R^4$ | $R^5$ | $ED_{50}$ mg/kg s.c. |
|---|---|---|---|---|
| H | H | H | H | 0.03 |
| H | 5-Cl | H | H | 0.05 |
| H | 5-CH$_3$ | H | H | 0.06 |
| CH$_3$ | H | H | H | 0.08 |
| CH$_2$=CH—CH$_2$ | H | H | H | 0.25 |
| H | H | H | 4-F | 0.04 |
| H | 5-Cl | H | 4-F | 0.015 |
| H | H | H | 3-CF$_3$ | 0.025 |
| H | H | CH$_3$ | H | 0.015 |

TABLE II

| L | $R^1$ | $R^2$ | $R^3$ | | $R^7$ | Salt and Solvate form | $ED_{50}$ mg/kg s.c. |
|---|---|---|---|---|---|---|---|
| H | H | H | H | N⟩ (piperidine) | H | — | 0.02 |
| H | 5-Cl | H | H | " | H | — | 0.10 |
| H | 5-CH$_3$ | 6-CH$_3$ | H | " | H | CH$_3$—CHOH—CH$_3$ | 0.45 |
| H | H | H | CH$_3$ | " | 5-Cl | — | 0.06 |
| H | H | H | H | " | 5-Cl | — | 0.01 |
| H | 5-Cl | H | H | " | 5-Cl | — | 0.12 |
| CH$_3$ | H | H | H | " | 5-Cl | — | 0.16 |
| CH$_2$=CH—CH$_2$ | H | H | H | " | 5-Cl | — | 0.12 |
| H | H | H | H | N⟩= (tetrahydropyridine) | H | — | 0.04 |
| H | 5-F | H | H | N⟩ (piperidine) | 5-Cl | HCl H$_2$O | 0.004 |

TABLE II-continued

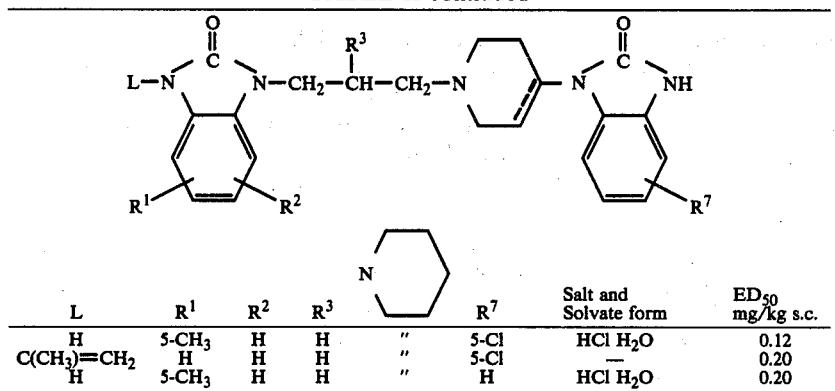

| L | $R^1$ | $R^2$ | $R^3$ | (piperidine) | $R^7$ | Salt and Solvate form | $ED_{50}$ mg/kg s.c. |
|---|---|---|---|---|---|---|---|
| H | 5-$CH_3$ | H | H | " | 5-Cl | HCl $H_2O$ | 0.12 |
| C($CH_3$)=$CH_2$ | H | H | H | " | 5-Cl | — | 0.20 |
| H | 5-$CH_3$ | H | H | " | H | HCl $H_2O$ | 0.20 |

TABLE III

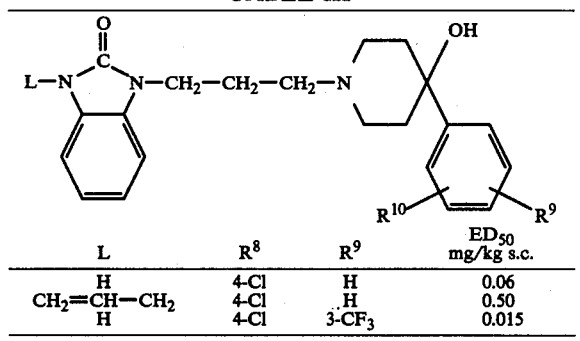

| L | $R^8$ | $R^9$ | $ED_{50}$ mg/kg s.c. |
|---|---|---|---|
| H | 4-Cl | H | 0.06 |
| $CH_2$=CH—$CH_2$ | 4-Cl | H | 0.50 |
| H | 4-Cl | 3-$CF_3$ | 0.015 |

TABLE IV

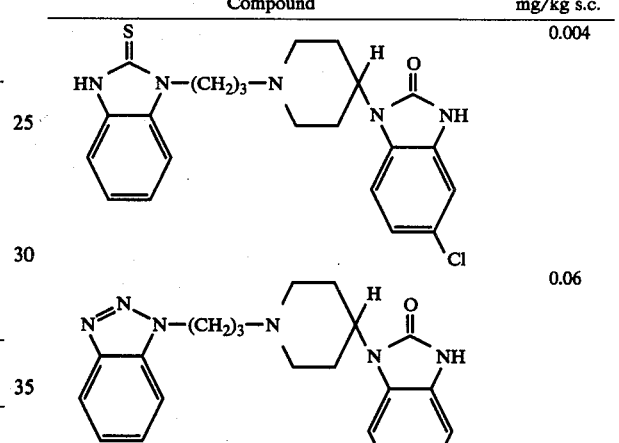

| Compound | $ED_{50}$ mg/kg s.c. |
|---|---|
| (benzimidazole-propyl-piperidine-anilinomethyl) | 0.25 |
| (benzothiazolone) | 0.001 |
| (benzoxazolone) | 0.03 |
| (benzimidazolethione) | 0.004 |
| (benzotriazole) | 0.06 |
| (benzimidazolone-thione) | 0.025 |
| (benzimidazolone with thione) | 0.004 |

In view of their useful antiemetic activity, the subject compounds may be formulated into various pharmaceutical forms for administration purposes. To prepare the pharmaceutical compositions of this invention, an effective antiemetic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. The amount of active ingredient per dosage unit will be from about 0.25 mg to about 100 mg and, preferably from about 1 to about 50 mg.

The following formulations exemplify typical antiemetic pharmaceutical compositions in dosage unit form suitable for systemic administration to animal and human subjects in accordance with the instant invention.

Oral drops: The following formulation provides 50 liters of an oral-drop solution comprising 10 milligrams of 5-chloro-1-{1-[3-(2,3-dihydro-2-oxo-1H-benzimidazol-1-yl)propyl]-4-piperidinyl}-1,3-dihydro-2H-benzimidazol-2-one as the active ingredient (A.I.) per milliliter.

| A.I. | 500 | grams |
| 2-hydroxypropanoic acid | 0.5 | liter |
| Sodium saccharin | 1750 | grams |
| Cocoa flavor | 2.5 | liters |
| Purified water | 2.5 | liters |
| Polyethylene glycol q.s. ad | 50 | liters. |

The A.I. is dissolved in the 2-hydroxypropanoic acid and 1.5 liters of the polyethylene glycol at 60°–80° C. After cooling to 30°–40° C. there are added 35 liters of polyethylene glycol and the mixture is stirred well. Then there is added a solution of the sodium saccharin in 2.5 liters of purified water and while stirring there are added the cocoa flavor and polyethylene glycol q.s. ad volume. The resulting solution is filled into suitable containers.

Injectable solution: The following formulation provides 20 liters of a parenteral solution comprising 2 milligrams of 5-chloro-1-{1-[3-(2,3-dihydro-2-oxo-1H-benzimidazol-1-yl)propyl]-4-piperidinyl}-1,3-dihydro-2H-benzimidazol-2-one as the active ingredient per milliliter.

| A.I. | 40 grams |
| 2,3-dihydroxybutanedioic acid | 20 grams |
| methyl 4-hydroxybenzoate | 36 grams |
| propyl 4-hydroxybenzoate | 4 grams |
| water for injection q.s. ad 20 liters | |

The methyl and propyl 4-hydroxybenzoates are dissolved in about 10 liters of boiling water for injection. After cooling to about 50° C. there are added while stirring the 2,3-dihydroxybutanedioic acid and thereafter the A.I.. The solution is cooled to room temperature and supplemented with water for injection q.s. ad volume. The solution is sterilized by filtration (U.S.P. XVII p. 811) and filled in sterile containers.

Oral solution: The following formulation provides 20 liters of an oral solution comprising 5 milligrams of 5-chloro-1-{1-[3-(2,3-dihydro-2-oxo-1H-benzimidazol-1-yl)propyl]-4-piperidinyl}-1,3-dihydro-2H-benzimidazol-2-one as the active ingredient per teaspoonful (5 milliliters).

| A.I. | 20 grams |
| 2,3-dihydroxybutanedioic acid | 10 grams |
| Sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad 20 liers. | |

The methyl and propyl 4-hydroxybenzoates are dissolved in 4 liters of boiling purified water. In 3 liters of this solution are dissolved first the 2,3-hydroxybutanedioic acid and thereafter the A.I.. The latter solution is combined with the remaining part of the former solution and the 1,2,3-propanetriol and the sorbitol solution are added thereto. The sodium saccharin is dissolved in 0.5 liters of water and the raspberry and gooseberry essences are added. The latter solution is combined with the former, water is added q.s. ad volume and the resulting solution is filled in suitable containers.

Film-coated tablets: 10,000 Compressed tablets, each containing as the active ingredient 10 milligrams of 5-chloro-1-{1-[3-(2,3-dihydro-2-oxo-1H-benzimidazol-1-yl)propyl]-4-piperidinyl}-1,3-dihydro-2H-benzimidazol-2-one, are prepared from the following formulation:

| Tablet core: | |
| A.I. | 100 grams |
| Lactose | 570 grams |
| Starch | 200 grams |
| Polyvinylpyrrolidone (Kollidon K 90) | 10 grams |
| Microcrystalline cellulose (Avicel) | 100 grams |
| Sodium dodecyl sulfate | 5 grams |
| Hydrogenated vegetable oil (Sterotex) | 15 grams |

| Coating: | | |
|---|---|---|
| Methyl cellulose (Methocel 60 HG) | 10 | grams |
| Ethyl cellulose (Ethocel 22 cps) | 5 | grams |
| 1,2,3-Propanetriol | 2.5 | milliliters |
| Polyethylene glycol 6000 | 10 | grams |
| Concentrated colour suspension (Opaspray K-1-2109) | 30 | milliliters |
| Polyvinylpyrrolidone (Povidone) | 5 | grams |
| Magnesium octadecanoate | 2.5 | grams |

Preparation of tablet core: A mixture of the A.I., the lactose and the starch is mixed well and thereafter humidified with a solution of the sodium dodecyl sulfate and the polyvinylpyrrolidone in about 200 milliliters of water. The wet powder mixture is sieved, dried and sieved again. Then there is added the microcrystalline cellulose and the hydrogenated vegetable oil. The whole is mixed well and compressed into tablets.

Coating: To a solution of the methyl cellulose in 75 milliliters of denaturated ethanol there is added a solution of the ethyl cellulose in 150 milliliters of dichloromethane. Then there are added 75 milliliters of dichloromethane and the 1,2,3-propanetriol. The polyethylene glycol is molten and dissolved in 75 milliliters of dichloromethane. The latter solution is added to the former and then there are added the magnesium octadecanoate, the polyvinylpyrrolidone and the concentrated colour suspension and the whole is homogenised.

The tablet cores are coated with the thus obtained mixture in a coating apparatus.

Suppositories: Hundred suppositories each containing 30 milligrams of 5-chloro-1-{-1-[3-(2,3-dihydro-2-oxo-1H-benzimidazol-1-yl)propyl]-4-piperidinyl}-1,3-dihydro-2H-benzimidazol-2-one as the active ingredient are prepared from the following formulations:

| A.I. | 3 | grams |
|---|---|---|
| 2,3-Dihydroxybutanedioic acid | 3 | grams |
| Polyethylene glycol 400 | 25 | milliliters |
| Surfactant (Span) | 12 | grams |
| Triglycerides (Witepsol 555) q.s. ad | 300 | grams |

The A.I. is dissolved in a solution of the 2,3-dihydroxybutanedioic acid in the polyethylene glycol 400. The surfactant and the triglycerides are molten together. The latter mixture is mixed well with the former solution. The thus obtained mixture is poured into moulds at a temperature of 37°–38° C. to form the suppositories.

In view of the antiemetic activity of the subject compounds, it is evident that the present invention provides a method of inhibiting emesis in warm-blooded animals by the systemic administration of an effective antiemetic amount of a compound of formula (I) and the pharmaceutically acceptable acid addition salts thereof in admixture with a pharmaceutical carrier.

The following examples are intended to illustrate but not to limit the scope of the present invention. Unless otherwise stated all parts therein are by weight.

EXAMPLE I

A mixture of 100 parts of 1-chloro-2-nitro-4-(trifluoromethyl)benzene, 90 parts of 3-amino-1-propanol and 200 parts of butanol is stirred and heated till reflux. Stirring at reflux is continued overnight. The reaction mixture is cooled and evaporated. Water is added to the residue and the whole is acidified with a hydrochloric acid solution. The product is extracted with methylbenzene. The extract is dried, filtered and evaporated. The solid residue is crystallized from petroleumether. The product is filtered off and dried, yielding 141 parts (100%) of 3-{[2-nitro-4-(trifluoromethyl)phenyl]amino}-1-propanol.

A mixture of 141 parts of 3-{[2-nitro-4-(trifluoromethyl)phenyl]amino}-1-propanol and 1200 parts of methanol is hydrogenated at normal pressure and at room temperature with 15 parts of Raney-nickel catalyst. After the calculated amount of hydrogen is taken up, the catalyst is filtered off and the filtrate is evaporated. The residue is crystallized from 2,2'-oxybispropane, yielding 110 parts (100%) of 3-{[2-amino-4-(trifluoromethyl)phenyl]amino}-1-propanol.

To a stirred mixture of 21 parts of 3-{[2-amino-4-(trifluoromethyl)phenyl]amino}-1-propanol and 100 parts of water are added 14.4 parts of hydrochloric acid solution. The whole is stirred for 10 minutes at room temperature. After cooling to 0°–10° C., there is added dropwise a solution of 18 parts of potassium cyanate in 50 parts of water. Upon completion, stirring is continued for 2 hours. The precipitated product is filtered off and dried. Then it is melted and the melt is stirred for 10 minutes. After cooling, it is dissolved in trichloromethane while heating. The solution is filtered and the product is allowed to crystallize from the filtrate. It is filtered off and dried, yielding 8 parts (34%) of 1,3-dihydro-1-(3-hydroxypropyl)-5-(trifluoromethyl)-2H-benzimidazol-2-one.

To a stirred mixture of 23 parts of 1,3-dihydro-1-(3-hydroxypropyl)-5-(trifluoromethyl)-2H-benzimidazol-2-one in 150 parts of trichloromethane are added dropwise 32 parts of sulfinyl chloride. Upon completion, the whole is heated to reflux and stirring is continued for 1 hour at reflux temperature. After cooling, the reaction mixture is evaporated and the residue is crystallized from 2,2'-oxybispropane, yielding 14 parts (56%) of 1-(3-chloropropyl)-1,3-dihydro-5-(trifluoromethyl)-2H-benzimidazol-2-one.

EXAMPLE II

A mixture of 171 parts of 1-chloro-4-methyl-2-nitrobenzene, 150 parts of 3-amino-1-propanol and 400 parts of butanol is stirred and refluxed for 30 hours. The reaction mixture is evaporated and the residue is poured onto water. The product is extracted with methylbenzene. The extract is washed with water and with a hydrochloric acid solution 2N, dried, filtered and evaporated. The residue is purified by column-chromatography over silica gel using a mixture of trichloromethane and 5% of methanol as eluent. The pure fractions are collected and the eluent is evaporated, yielding 70 parts (33%) of 3-[(4-methyl-2-nitrophenyl)amino]-1-propanol as a residue.

A mixture of 70 parts of 3-[(4-methyl-2-nitrophenyl)amino]-1-propanol and 400 parts of methanol is hydrogenated at normal pressure and at room temperature with 10 parts of palladium-on-charcoal catalyst 10%. After the calculated amount of hydrogen is taken up, the catalyst is filtered off and the filtrate is evaporated, yielding 54 parts (91%) of 3-[(2-amino-4-methylphenyl)amino]-1-propanol as a residue.

To a stirred and cooled solution of 54 parts of 3-[(2-amino-4-methylphenyl)amino]-1-propanol in 30 parts of hydrochloric acid solution 10% and 200 parts of water is added dropwise a solution of 28 parts of potassium cyanate in 50 parts of water at a temperature below 10° C. Upon completion, stirring is continued first for 1 hour at room temperature and further for 24 hours at reflux temperature. After cooling to room temperature, the product is extracted with trichloromethane. The extract is washed with a hydrochloric acid solution 5%, dried, filtered and evaporated. The residue is crystallized from 4-methyl-2-pentanone, yielding 19.5 parts (31%) of 1,3-dihydro-1-(3-hydroxypropyl)-5-methyl-2H-benzimidazol-2-one; mp. 114.1° C.

To a stirred solution of 18.5 parts of 1,3-dihydro-1-(3-hydroxypropyl)-5-methyl-2H-benzimidazol-2-one in 325 parts of dichloromethane are added 11.9 parts of N,N-diethylethanamine. Then there are added dropwise (slowly) 11.5 parts of methanesulfonyl chloride. Upon completion, stirring is continued for 1 hour at reflux temperature. After cooling, the reaction mixture is washed with water, dried, filtered and evaporated. The solid residue is crystallized from 4-methyl-2-pentanone, yielding 15 parts (58%) of 1,3-dihydro-1-(3-hydroxypropyl)-5-methyl-2H-benzimidazol-2-one methanesulfonate; mp. 125° C.

EXAMPLE III

A mixture of 113.2 parts of 1,2,4-trichloro-5-nitrobenzene, 75 parts of 3-amino-1-propanol, 0.2 parts of potassium iodide and 200 parts of butanol is stirred and refluxed overnight. The butanol is removed by evaporation in vacuo and water is added to the residue. The product is extracted with 4-methyl-2-pentanone. The extract is washed a few times with water, dried, filtered and evaporated. The oily residue is purified by column-chromatography over silica gel using a mixture of trichloromethane and 5% of methanol as eluent. The pure fractions are collected and the eluent is evaporated. The residue is triturated in 2,2'-oxybispropane. The product is filtered off and crystallized from a mixture of 2,2'-oxybispropane and 2-propanol, yielding 31.7 parts of 3-[(4,5-dichloro-2-nitrophenyl)amino]-1-propanol; mp. 97° C.

A mixture of 39.7 parts of 3-[(4,5-dichloro-2-nitrophenyl)amino]-1-propanol and 400 parts of methanol is hydrogenated at normal pressure and at room temperature with 5 parts of Raney-nickel catalyst. After the calculated amount of hydrogen is taken up, the catalyst is filtered off. The filtrate is acidified with 24 parts of a hydrochloric acid solution while stirring. The solvent is evaporated and the solid residue is stirred in 2-propanol. The product is filtered off and dried in vacuo, yielding 31.5 parts of 3-[(2-amino-4,5-dichlorophenyl)amino]-1-propanol hydrochloride; mp. 185° C.

To a stirred mixture of 31.2 parts of 3-[(2-amino-4,5-dichlorophenyl)amino]-1-propanol hydrochloride in 200 parts of water is added dropwise, during a 15 minutes-period, a solution of 10.6 parts of potassium cyanate in 50 parts of water at a temperature between 15° and 20° C. Upon completion, stirring is continued first for 20 minutes at room temperature and further for 20 hours at reflux. The reaction mixture is allowed to cool over week-end to room temperature. The precipitated product is filtered off and boiled in trichloromethane. The undissolved part is filtered off and boiled in 4-methyl-2-pentanone. After cooling, the product is filtered off and dried, yielding 14.5 parts (48%) of 5,6-dichloro-1,3-dihydro-1-(3-hydroxypropyl)-2H-benzimidazol-2-one; mp. 174.7° C. To a stirred mixture of 13.3 parts of 5,6-dichloro-1,3-dihydro-1-(3-hydroxypropyl)-2H-benzimidazol-2-one, 8 parts of N,N-diethylethanamine and 260 parts of dichloromethane are added dropwise 7.4 parts of methanesulfonyl chloride. Upon completion, stirring is continued for one hour at reflux temperature. The reaction mixture is washed with water, dried, filtered and evaporated. The solid residue is shaken with acidified water and 4-methyl-2-pentanone. The whole is filtered (the filtrate is set aside) and the filter-cake is dried, yielding a first fraction of 6.2 parts of 5,6-dichloro-1,3-dihydro-1-(3-hydroxypropyl)-2H-benzimidazol-2-one methanesulfonate. The 4-methyl-2-pentanone-phase is separated from the filtrate, dried, filtered and evaporated, yielding a second fraction of 8 parts of 5,6-dichloro-1,3-dihydro-1-(3-hydroxypropyl)-2H-benzimidazol-2-one methanesulfonate as an oily residue.

EXAMPLE IV

A mixture of 100 parts of 1,2-dichloro-3-nitrobenzene, 95 parts of 3-amino-1-propanol and 200 parts of butanol is stirred and refluxed overnight. The reaction mixture is cooled and evaporated. The residue is taken up in water and the product is extracted with methylbenzene. The extract is washed with water, dried, filtered and evaporated, yielding 115 parts of 3-[(2-chloro-6-nitrophenyl)amino]-1-propanol as a residue.

A mixture of 115 parts of 3-[(2-chloro-6-nitrophenyl)amino]-1-propanol and 400 parts of ethanol is hydrogenated at normal pressure and at room temperature with 12 parts of a Raney-nickel catalyst. After the calculated amount of hydrogen is taken up, the catalyst is filtered off and the filtrate is evaporated. The residue is purified by column-chromatography over silica gel using a mixture of trichloromethane and 5% of methanol as eluant. The pure fractions are collected and the eluent is evaporated, yielding 20 parts (20%) of 3-[(2-amino-6-chlorophenyl)amino]-1-propanol as a residue.

To a stirred and cooled (10° C.) mixture of 20 parts of 3-[(2-amino-6-chlorophenyl)amino]-1-propanol, 12 parts of a hydrochloric acid solution and 100 parts of water is added dropwise a solution of 9 parts of potassium cyanate in 30 parts of water. Upon completion, stirring is continued first for 2 hours at room temperature and further overnight at reflux temperature. After cooling, the product is extracted with trichloromethane. The extract is washed with a diluted hydrochloric acid solution, dried, filtered and evaporated. The residue is crystallized from 4-methyl-2-pentanone, yielding 9 parts (41%) of 4-chloro-1,3-dihydro-3-(3-hydroxypropyl)-2H-benzimidazol-2-one.

To a stirred mixture of 9 parts of 4-chloro-1,3-dihydro-3-(3-hydroxypropyl)-2H-benzimidzol-2-one, 7 parts of N,N-diethylethanamine and 130 parts of dichloromethane are added dropwise 12 parts of methanesulfonyl chloride (exothermic reaction: temperature rises to reflux). Upon completion, stirring is continued for 1 hour at reflux temperature. The reaction mixture is cooled and poured onto water. The organic phase is separated, washed with acidified water, dried, filtered and evaporated. The residue is crystallized from 4-methyl-2-pentanone, yielding 9 parts (75%) of 4-chloro-1,3-dihydro-3-(3-hydroxypropyl)-2H-benzimidazol-2-one methanesulfonate.

EXAMPLE V

A mixture of 34.6 parts of 3-[(4-chloro-2-nitrophenyl)-amino]-1-propanol and 320 parts of ethanol is hydrogenated at normal pressure and at room temperature with 8 parts of Raney-nickel catalyst. After the calculated amount of hydrogen is taken up, the catalyst is filtered off and the filtrate is evaporated, yielding 30 parts of 3-[(2-amino-4-chlorophenyl)amino]-1-propanol as an oily residue.

To a stirred solution of 40 parts of 3-[(2-amino-4-chlorophenyl)amino]-1-propanol in 140 parts of water and 24 parts of a hydrochloric acid solution 10N is added dropwise a solution of 18 parts of potassium isocyanate in 40 parts of water (exothermic reaction: temperature rises to 35° C.). Upon completion, stirring is continued first for 30 minutes at room temperature and further for 20 hours at reflux temperature. The reaction mixture is allowed to stir over week-end without heating. The precipitated product is filtered off and treated with a diluted hydrochloric acid solution in 4-methyl-2-pentanone. The whole is stirred and the layers are separated. The 4-methyl-2-pentanone-phase is washed with water, dried, filtered and evaporated, yielding 18 parts (32%) of 5-chloro-1,3-dihydro-1-(3-hydroxypropyl)-2H-benzimidazol-2-one; mp. 148.8° C.

To a stirred and cooled (ice-water bath) mixture of 14.1 parts of 5-chloro-1,3-dihydro-1-(3-hydroxypropyl)-2H-benzimidazol-2-one, 8 parts of N,N-diethylethanamine and 195 parts of dichloromethane are added dropwise 7.8 parts of methanesulfonyl chloride. Upon completion, stirring is continued first for 15 minutes while still cooling an further for 1 hour at reflux temperature. The dichloromethane is evaporated and the residue is dissolved in 4-methyl-2-pentanone and water while heating. The layers are separated and the organic phase is stirred with 100 parts of water, while cooling in an ice-bath. The precipitated product is filtered off and dried, yielding 10 parts (53%) of 5-chloro-1,3-dihydro-1-(3-hydroxypropyl)-2H-benzimidazol-2-one methanesulfonate; mp. 140° C.

EXAMPLE VI

A mixture of 20 parts of 5-chloro-1,3-dihydro-1-(3-hydroxypropyl)-2H-benzimidazol-2-one, 34 parts of sulfinyl chloride and 300 parts of trichloromethane is stirred and refluxed for 4 hours. The trichloromethane is evaporated and the residue is crystallized from 4-methyl-2-pentanone (activated charcoal). The product is filtered off (the filtrate is set aside), yielding a first fraction of 8.2 parts of 5-chloro-1-(3-chloropropyl)-1,3-dihydro-2H-benzimidazol-2-one. The filtrate, which was set aside, is concentrated and the concentrate is stirred with 2,2′-oxybispropane. The precipitated product is filtered off and dried, yielding a second fraction of 8 parts of 5-chloro-1-(3-chloropropyl)-1,3-dihydro-2H-benzimidazol-2-one.

EXAMPLE VII

To a stirred mixture of 22.6 parts of 6-chloro-1,3-dihydro-1-(3-hydroxypropyl)-2H-benzimidazol-2-one and 300 parts of trichloromethane are added dropwise 32 parts of sulfinyl chloride. Upon completion, stirring is continued for 3 hours at reflux. After stirring with activated charcoal, the reaction mixture is filtered hot over hyflo. The filtrate is evaporated and the residue is dissolved in methylbenzene. The solution is washed a few times with water, dried, filtered and evaporated. The oily residue is triturated in 2,2′-oxybispropane. The solid product is filtered off and dried, yielding 19 parts (77.5%) of 6-chloro-1-(3-chloropropyl)-1,3-dihydro-2H-benzimidazol-2-one; mp. 122° C.

EXAMPLE VIII

To a stirred and heated mixture of 17.5 parts of 1,3-dihydro-1-(2-propenyl)-2H-benzimidazol-2-one, 5 parts of N,N,N-triethylbenzenemethanaminium chloride and 150 parts of a sodium hydroxide solution 60% are added dropwise 20.5 parts of 1-bromo-3-chloropropane at 60° C. Upon completion, stirring at 60° C. is continued for 5 hours. The reaction mixture is cooled, water is added and the product is extracted with trichloromethane. The extract is dried, filtered and evaporated, yielding 21 parts (84%) of 1-(3-chloropropyl)-1,3-dihydro-3-(2-propenyl)-2H-benzimidazol-2-one as a residue.

EXAMPLE IX

To a stirred solution of 8.5 parts of 1,3-dihydro-1-(1-methylethenyl)-2H-benzimidazol-2-one in 45 parts of N,N-dimethylformamide are added portionwise 1.7 parts of a sodium hydride dispersion 78%. After stirring for 1 hour at room temperature, the whole is cooled to 0°–5° C. and 8.65 parts of 1-bromo-3-chloropropane are added dropwise (slowly). Upon completion, stirring is continued for 3 hours at room temperature. The reaction mixture is poured onto crushed ice and the product is extracted with methylbenzene. The extract is washed with water, dried, filtered and evaporated. The residue is crystallized from 2-propanol, yielding 5.5 parts (44%) of 1-(3-chloropropyl)-1,3-dihydro-3-(1-methylethenyl)-2H-benzimidazol-2-one; mp. 115° C.

A solution of 13 parts of 1-(3-chloropropyl)-1,3-dihydro-3-(1-methylethenyl)-2H-benzimidazol-2-one in 6 parts of a hydrochloric acid solution and 40 parts of ethanol is stirred for 2 hours at room temperature. The reaction mixture is evaporated and the solid residue is crystallized from 2-propanol, yielding 9.5 parts (90%) of 1-(3-chloropropyl)-1,3-dihydro-2H-benzimidazol-2-one; mp. 115° C.

EXAMPLE X

To a stirred and hot (55° C.) mixture of 22.2 parts of 1,3-dihydro-5,6-dimethyl-3-(1-methyl-2-phenylethenyl)-2H-benzimidazol-2-one, 3 parts of N,N,N-triethylbenzenemethanaminium chloride and 112.5 parts of a sodium hydroxide solution 60% are added dropwise 15.8 parts of 1-bromo-3-chloropropane (slightly exothermic reaction). Upon completion, stirring is continued for 5 hours at 55° C. After cooling, water is added and the oily product is extracted with methylbenzene. The extract is dried, filtered and evaporated. The residue is crystallized from 2,2′-oxybispropane, yielding, after drying, 25 parts (88.5%) of 1-(3-chloropropyl)-1,3-dihydro-5,6-dimethyl-3-(1-methyl-2-phenylethenyl)-2H-benzimidazol-2-one; mp. 98° C.

A mixture of 25 parts of 1-(3-chloropropyl)-1,3-dihydro-5,6-dimethyl-3-(1-methyl-2-phenylethenyl)-2H-benzimidazol-2-one, 165 parts of a hydrochloric acid solution 6N and 160 parts of ethanol is stirred and refluxed for 6 hours. The reaction mixture is evaporated and the residue is dissolved in trichloromethane. This solution is dried, filtered and evaporated. The residue is crystallized from a mixture of 2,2′-oxybispropane and 2-propanol, yielding, after drying, 16 parts (94.7%) of 1-(3-chloropropyl)-1,3-dihydro-5,6-dimethyl-2H-benzimidazol-2-one; mp. 140° C.

EXAMPLE XI

A solution of 180 parts of 3-[(2-nitrophenyl)amino]-1-propanol in 200 parts of methanol and 100 parts of a hydrochloric acid solution 10N is hydrogenated at normal pressure and at a temperature at 50° C., in the presence of 5 parts of palladium-on-charcoal catalyst 10%. After the calculated amount of hydrogen (3 moles) is taken up, hydrogenation is stopped. The catalyst is filtered off and the filtrate is evaporated. The residue (mainly 3-[(2-aminophenyl)amino]-1-propanol hydrochloride) is dissolved in 500 parts of water. To this solution is added a solution of 88.8 parts of potassium isocyanate in 150 parts of water and the whole is stirred and refluxed for 15 hours. The reaction mixture is cooled and the product is extracted with trichloromethane. The extract is dried and evaporated. The residue is dissolved in 250 parts of boiling water, treated with activated charcoal and crystallized at room temperature. The precipitate is filtered off and recrystallized from 400 parts of water, followed by recrystallization from ethyl acetate, yielding 58 parts of 1,3-dihydro-1-(3-hydroxypropyl)-2H-benzimidazol-2-one hydrate; mp. 48°–65° C.

To a solution of 52.5 parts of 1,3-dihydro-1-(3-hydroxypropyl)-2H-benzimidazol-2-one hydrate in 200 parts of pyridine is added dropwise 63 parts of methanesulfonyl chloride. The mixture is stirred and cooled on the air for 2 hours. The pyridine is evaporated. To the residue is added 500 parts of water and the formed precipitate is filtered off. It is dissolved in 350 parts of trichloromethane. This solution is dried over magnesium sulfate and evaporated. The residue is crystallized from 40 parts of methylbenzene, yielding 25.5 parts of 1,3-dihydro-1-(3-hydroxypropyl)-2H-benzimidazol-2-one methanesulfonate; mp. 118°–120° C.

To a solution of 0.5 parts of sodium in 40 parts of absolute ethanol are added in the cold 5.4 parts of 1,3-dihydro-1-(3-hydroxypropyl)-2H-benzimidazol-2-one methanesulfonate. The whole is stirred until all solid enters solution. The solution is further stirred and refluxed for 2 hours. After cooling, the reaction mixture is filtered from some inorganic matter and the filtrate is evaporated. The residue is dissolved in 80 parts of methylbenzene, boiled with activated charcoal, filtered and the filtrate is evaporated again. The solid residue is washed with cold methylbenzene and crystallized from 16 parts of methylbenzene, yielding 2.6 parts of 3,4-dihydro-2H-[1,3]oxazino[3,2-a]benzimidazole; mp. 116.5°–118.5° C.

To a solution of 5.7 parts of 3,4-dihydro-2H-[1,3]oxazino[3,2-a]benzimidazole in 80 parts of 2-propanone is added 5.7 parts of iodomethane and the whole is stirred and refluxed for 2h. 50. Then there is added a second portion of 5.7 parts of iodomethane and the whole is further stirred and refluxed for 2H. 50. The solvent is evaporated, yielding 1,3-dihydro-1-(3-iodopropyl)-3-methyl-2H-benzimidazol-2-one as an oily residue.

EXAMPLE XII

To a stirred mixture of 17.4 parts of 1,3-dihydro-1-(1-methylethenyl)-2H-benzimidazol-2-one, 5 parts of N,N,N-triethylbenzenemethanaminium chloride and 180 parts of sodium hydroxide solution 60% are added dropwise 21 parts of 1-bromo-3-chloro-2-methylpropane while heating at 55° C. Upon completion, stirring at 55° C. is continued for 3 hours. The reaction mixture is cooled, poured onto water and the product is extracted with methylbenzene. The extract is dried, filtered and evaporated, yielding 24 parts (90.6%) of 1-(3-chloro-2-methylpropyl)-1,3-dihydro-3-(1-methylethenyl)-2H-benzimidazol-2-one as a residue.

A mixture of 12 parts of 1-(3-chloro-2-methylpropyl)-1,3-dihydro-3-(1-methylethenyl)-2H-benzimidazol-2-one, 5 parts of sodium carbonate, 0.1 parts of potassium iodide and 200 parts of 4-methyl-2-pentanone is stirred and refluxed for 20 hours with water-separator. After cooling, water is added and the layers are separated. The organic phase is dried, filtered and evaporated, yielding 7 parts (72.9%) of 5-chloro-1-[1-{3-[1,3-dihydro-3-(1-methylethenyl)-2-oxo-2H-benzimidazol-1-yl]-2-methylpropyl}-4-piperidinyl]-1,3-dihydro-2H-benzimidazol-2-one as an oily residue.

EXAMPLE XIII

A mixture of 4.6 parts of 1-(3-chloropropyl)-1,3-dihydro-2H-benzimidazol-2-one, 5 parts of 1-(p-fluorophenyl)-1,3,8-triazaspiro[4,5]decan-4-one, 10 parts of sodium carbonate, 0.2 parts of potassium iodide and 80 parts of 4-methyl-2-pentanone is stirred and refluxed overnight. After cooling, the precipitated product is filtered off and triturated twice: first in a boiling mixture of 4-methyl-2-pentanone and 2-propanol and then in boiling methanol. It is filtered off again and crystallized from a mixture of N,N-dimethylformamide and water, yielding 4.5 parts of 8-[3-(1,3-dihydro-2-oxo-2H-benzimidazol-1-yl)propyl]-1-(4-fluorophenyl)-1,3,8-triazaspiro[4,5]decan-4-one; mp. 215.4° C.

EXAMPLE XIV

Following the procedure of Example XIII and using therein equivalent amounts of the appropriate starting materials, the following compounds are obtained:
8-[3-(6-chloro-1,3-dihydro-2-oxo-2H-benzimidazol-1-yl)propyl]-1-(4-fluorophenyl)-1,3,8-triazaspiro[4,5]decan-4-one hemihydrate; mp. 233° C.;
1-(4-fluorophenyl)-8-[3-(1,3-dihydro-5,6-dimethyl-2-oxo-2-H-benzimidazol-1-yl)propyl]-1,3,8-triazaspiro[4,5]decan-4-one; mp. 245° C.;
8-{3-[1,3-dihydro-2-oxo-3-(2-propenyl)-2H-benzimidazol-1-yl]propyl}-1-phenyl-1,3,8-triazaspiro[4,5]decan-4-one; mp. 114° C.; and
8-[3-(2,3-dihydro-2-oxo-1H-benzimidazol-1-yl)propyl]-1-[3-(trifluoromethyl)phenyl]-1,3,8-triazaspiro[4,5]decan-4-one; mp. 198.2° C.

EXAMPLE XV

A mixture of 2.3 parts of 1-(3-chloropropyl)-1,3-dihydro-2H-benzimidazol-2-one, 2.31 parts of 1-phenyl-1,3,8-triazaspiro[4,5]decan-4-one, 3.2 parts of sodium carbonate, 0.1 parts of potassium iodide and 80 parts of 4-methyl-2-pentanone is stirred and refluxed overnight. After cooling to room temperature, water is added. The undissolved product is filtered off and purified by column-chromatography over silica gel using a mixture of trichloromethane and 10% of methanol as eluent. The pure fractions are collected and the eluent is evaporated, yielding 0.9 parts (22%) of 8-[3-(1,3-dihydro-2-oxo-2H-benzimidazol-1-yl)propyl]-1-phenyl-1,3,8-triazaspiro[4,5]decan-4-one; mp. 228° C.

EXAMPLE XVI

Following the procedure of Example XV and using therein equivalent amounts of the appropriate starting materials, the following compounds are obtained:
8-[3-(5-chloro-1,3-dihydro-2-oxo-2H-benzimidazol-1-yl)propyl]-1-(4-fluorophenyl)-1,3,8-triazaspiro[4,5]decan-4-one; mp. 171.7° C.;
8-[3-(6-chloro-1,3-dihydro-2-oxo-2H-benzimidazol-1-yl)propyl]-1-phenyl-1,3,8-triazaspiro[4,5]decan-4-one; mp. 255°–256° C.; and
1-(4-fluorophenyl)-8-{3-[1,3-dihydro-2-oxo-5-(trifluoromethyl)-2H-benzimidazol-1-yl]-propyl}-1,3,8-triazaspiro[4,5]decan-4-one; mp. 259.7° C.

EXAMPLE XVII

A mixture of 4.8 parts of 1-(3-chloropropyl)-1,3-dihydro-2H-benzimidazol-2-one, 5.6 parts of 3-methyl-1-phenyl-1,3,8-triazaspiro[4,5]decan-4-one hydrochloride, 7.4 parts of sodium carbonate and 200 parts of 4-methyl-2-pentanone is stirred and refluxed overnight with water-separator. The reaction mixture is cooled, water is added and the layers are separated. The 4-methyl-2-pentanone-phase is dried, filtered and evaporated. The residue is purified by column-chromatography over silica gel using a mixture of trichloromethane and 5% of methanol as eluent. The pure fractions are collected and the eluent is evaporated. The residue is triturated in 4-methyl-2-pentanone. The solid product is filtered off and dried, yielding 4.1 parts (50%) of 8-[3-(1,3-di-hydro-2-oxo-2H-benzimidazol-1-yl)propyl]-3-methyl-1-phenyl-1,3,8-triazaspiro[4,5]decan-4-one; mp. 186° C.

EXAMPLE XVIII

A mixture of 4.2 parts of 4-chloro-1,3-dihydro-3-(3-hydroxypropyl)-2H-benzimidazol-2-one methanesulfonate, 2.5 parts of 1-phenyl-1,3,8-triazaspiro[4,5]decan-4-one, 10 parts of sodium carbonate and 80 parts of 4-methyl-2-pentanone is stirred and refluxed overnight. The reaction mixture is cooled and water is added. The precipitated product is filtered off and crystallized twice from a mixture of N,N-dimethylformamide and water, yielding 0.8 parts (17%) of 8-[3-(7-chloro-1,3-dihydro-2-oxo-2H-benzimidazol-1-yl)propyl]-1-phenyl-1,3,8-triazaspiro[4,5]decan-4-one; mp. 258.4° C.

EXAMPLE XIX

A mixture of 4.9 parts of 5-chloro-1,3-dihydro-2-oxo-2H-benzimidazole-1-propanol methanesulfonate, 3.7 parts of 1-phenyl-1,3,8-triazaspiro[4,5]decan-4-one, 3.4 parts of sodium carbonate and 90 parts of N,N-dimethylformamide is stirred and heated for 1 hour at 50°–60° C. The N,N-dimethylformamide is distilled off and the residue is taken up in water. The product is extracted with 4-methyl-2-pentanone. The extract is dried, filtered and evaporated. The residue is purified by column-chromatography over silica gel using a mixture of trichloromethane and 10% of methanol as eluent. The pure fractions are collected and the eluent is evaporated. The residue solidifies on triturating in 4-methyl-2-pentanone. The product is filtered off and crystallized twice: first from 2-propanol and then from a mixture of N,N-dimethylformamide and water, yielding 1.8 parts (25%) of 8-[3-(5-chloro-1,3-dihydro-2-oxo-2H-benzimidazol-1-yl)propyl]-1-phenyl-1,3,8-triazaspiro[4,5]decan-4-one; mp. 233.7° C.

EXAMPLE XX

A mixture of 5.68 parts of 1,3-dihydro-1-(3-hydroxypropyl)-5-methyl-2H-benzimidazol-2-one methanesulfonate, 4.62 parts of 1-phenyl-1,3,8-triazaspiro[4,5]decan-4-one, 3.7 parts of sodium carbonate and 45 parts of N,N-dimethylformamide is stirred for 1 hour at 60° C. The reaction mixture is cooled and poured onto water. The precipitated product is filtered off and purified by column-chromatography over silica gel using a mixture of trichloromethane and 10% of methanol as eluent. The pure fractions are collected and the eluent is evaporated. The residue is crystallized from a mixture of N,N-dimethylformamide and water, yielding 2 parts (24%) of 8-[3-(1,3-dihydro-5-methyl-2-oxo-2H-benzimidazol-1-yl)propyl]-1-phenyl-1,3,8-triazaspiro[4,5]decan-4-one; mp. 255.5° C.

EXAMPLE XXI

A mixture of 5 parts of 1,3-dihydro-1-(3-iodopropyl)-3-methyl-2H-benzimidazol-2-one, 3.4 parts of 1-phenyl-1,3,8-triazaspiro[4,5]decan-4-one, 2.65 parts of sodium carbonate and 22.5 parts of N,N-dimethylformamide is stirred and heated for 2 hours at 70° C. The reaction mixture is cooled and poured onto water, whereupon an oily precipitate is formed. The supernatant aqueous phase is decanted and the residual oil is dissoved in trichloromethane. The solution is dried, filtered and evaporated. The residue is purified by column-chromatography over silica gel using a mixture of trichloromethane and 5% of methanol as eluent. The pure fractions are collected and the eluent is evaporated, yielding 1 part of 8-[3-(1,3-dihydro-3-methyl-2-oxo-2H-benzimidazol-1-yl)propyl]-1-phenyl-1,3,8-triazaspiro[4,5]decan-4-one; mp. 164.4° C.

EXAMPLE XXII

A mixture of 8 parts of 5,6-dichloro-1,3-dihydro-1-(3-hydroxypropyl)-2H-benzimidazol-2-one methanesulfonate, 9.2 parts of 1-phenyl-1,3,8-triazaspiro[4,5]decan-4-one and 90 parts of N,N-dimethylformamide is stirred and heated at 60° C. for one hour. The reaction mixture is evaporated and water is added to the residue. The whole is alkalized with ammonium hydroxide and the product is extracted with trichloromethane. The extract is dried, filtered and evaporated. The residue is purified by column-chromatography over silica gel using a mixture of trichloromethane and 10% of methanol as eluent. The pure fractions are collected and the eluent is evaporated. The solid residue is triturated in 4-methyl-2-pentanone. The product is filtered off and dried, yielding 2 parts of 8-[3-(5,6-dichloro-1,3-dihydro-2-oxo-2H-benzimidazol-1-yl)propyl]-1-phenyl-1,3,8-triazaspiro[4,5]decan-4-one; mp. 275.2° C.

EXAMPLE XXIII

A mixture of 2.3 parts of 1-(3-chloropropyl)-1,3-dihydro-2H-benzimidazol-2-one, 2.5 parts of 5-chloro-1,3-dihydro-1-(4-piperidinyl)-2H-benzimidazol-2-one, 3.2 parts of sodium carbonate, 0.1 parts of potassium iodide and 80 parts of 4-methyl-2-pentanone is stirred and refluxed for 24 hours. The reaction mixture is cooled to room temperature and water is added. The undissolved product is filtered off and purified by column-chromatography over silica gel using a mixture of trichloromethane and 10% of methanol is eluent. The pure fractions are collected and the eluent is evaporated. The residue is crystallized from 4-methyl-2-pentanone. The product is filtered off and recrystallized from a mixture of N,N-dimethylformamide and water, yielding 1.3 parts (30%) of 5-chloro-1-{1-[3-(1,3-dihydro-2-oxo-2H-benzimidazol-1-yl)propyl]-4-piperidinyl}-1,3-dihydro-2H-benzimidazol-2-one; mp. 242.5° C.

EXAMPLE XXIV

A mixture of 5.4 parts of 6-chloro-1-(3-chloropropyl)-1,3-dihydro-2H-benzimidazol-2-one, 5 parts of 5-chloro-1,3-dihydro-1-(4-piperidinyl)-2H-benzimidazol-2-one, 6.4 parts of sodium carbonate, 0.2 parts of potassium iodide and 200 parts of 4-methyl-2-pentanone is stirred and refluxed overnight with water-separator. After cooling, water is added and the layers are separated. The 4-methyl-2-pentanone-phase is dried, filtered and evaporated. The oily residue is purified by column-chromatography over silica gel using a mixture of trichloromethane and 10% of methanol as eluent. The pure fractions are collected and the eluent is evaporated. The solid residue is crystallized from a mixture of N,N-dimethylformamide and water, yielding 2 parts (22%) of 6-chloro-1-{3-[4-5(chloro-1,3-dihydro-2-oxo-2H-benzimidazol-1-yl)-1-piperidinyl]propyl}-1,3-dihydro-2H-benzimidazol-2-one hydrate; mp. 179.6° C.

EXAMPLE XXV

A mixture of 3.58 parts of 1-(3-chloropropyl)-1,3-dihydro-5,6-dimethyl-2H-benzimidazol-2-one, 3.26 parts of 1,3-dihydro-1-(4-piperidinyl)-2H-benzimidazol-2-one, 5.3 parts of sodium carbonate, 0.2 parts of potassium iodide and 200 parts of 4-methyl-2-pentanone is stirred and refluxed for 24 hours with water-separator. After cooling, water is added and the layers are separated. The organic phase is dried, filtered and evaporated. The residue is crystallized from 2-propanol, yielding, after drying, 2.5 parts of 1-{3-[4-(1,3-dihydro-2-oxo-2H-benzimidazol-1-yl)-1-piperidinyl]propyl}-1,3-dihydro-5,6-dimethyl-2H-benzimidazol-2-one 2-propanolate; mp. 159° C.

EXAMPLE XXVI

A mixture of 5.6 parts of 6-chloro-1-(3-chloropropyl)-1,3-dihydro-2H-benzimidazol-2-one, 4.34 parts of 1,3-dihydro-1-(4-piperidinyl)-2H-benzimidazol-2-one, 6.4 parts of sodium carbonate, 0.2 parts of potassium iodide and 200 parts of 4-methyl-2-pentanone is stirred and refluxed overnight with water-separator. The reaction mixture is cooled and water is added. The undissolved product is filtered off and crystallized from a mixture of N,N-dimethylformamide and water. It is filtered off again, boiled in methanol, filtered off while hot and dried, yielding 5.1 parts of 6-chloro-1,3-dihydro-1-{3-[4-(1,3-dihydro-2-oxo-2H-benzimidazol-1-yl)-1-piperidinyl]propyl}-2H-benzimidazol-2-one; mp. 273° C.

EXAMPLE XXVII

Following the procedure of Example XXVI and using therein equivalent amounts of the appropriate starting materials, the following compounds are obtained:

1-{3-[4-(1,3-dihydro-2-oxo-2H-benzimidazol-1-yl)-1-piperidinyl]propyl}-1,3-dihydro-2H-benzimidazol-2-one; mp. 225° C.;

1,3-dihydro-1-{3-[4-(1,3-dihydro-2-oxo-2H-benzimidazol-1-yl)-1-piperidinyl]propyl}-5-(trifluoromethyl)-2H-benzimidazol-2-one; mp. 263.4° C.;

5-chloro-1-{3-[4-(1,3-dihydro-2-oxo-2H-benzimidazol-1-yl)-1-piperidinyl]propyl}-1,3-dihydro-2H-benzimidazol-2one; mp. 253°-255° C.; and 5-chloro-1-[1-{3-[1,3-dihydro-2-oxo-3-(2-propenyl)-2H-benzimidazol-1-yl]propyl}-4-piperidinyl]-1,3-dihydro-2H-benzimidazol-2-one; mp. 153.4° C.

EXAMPLE XXVIII

A mixture of 5 parts of 1,3-dihydro-1-(3-iodopropyl)-3-methyl-2H-benzimidazol-2-one, 3.75 parts of 5-chloro-1,3-dihydro-1-(4-piperidinyl)-2H-benzimidazol-2-one, 2.65 parts of sodium carbonate and 22.5 parts of N,N-dimethylformamide is stirred at 70°-80° C. for 2 hours. The reaction mixture is cooled, poured onto water and the precipitated product is filtered off. It is dissolved in trichloromethane. The solution is dried, filtered and evaporated. The residue is crystallized from 4-methyl-2-pentanone, yielding 3 parts (43%) of 5-chloro-1-{1-[3-(1,3-dihydro-3-methyl-2-oxo-2H-benzimidazol-1-yl)propyl]-4-piperidinyl}-1,3-dihydro-2H-benzimidazol-2-one; mp. 166.5° C.

EXAMPLE XXIX

A mixture of 7.6 parts of 5-chloro-1,3-dihydro-1-(3-hydroxypropyl)-2H-benzimidazol-2-one methanesulfonate, 5.5 parts of 5-chloro-1,3-dihydro-1-(4-piperidinyl)-2H-benzimidazol-2-one, 5 parts of sodium carbonate and 63 parts of N,N-dimethylformamide is stirred and heated in an oil-bath at 50°-60° C. for 2 hours. The reaction mixture is poured onto water. The precipitated product is filtered off, dried and purified by column-chromatography over silica gel using a mixture of trichloromethane and 10% of methanol as eluent. The pure fractions are collected and the eluent is evaporated. The solid residue is crystallized from 4-methyl-2-pentanone. The product is filtered off and recrystallized from a mixture of N,N-dimethylformamide and water. It is filtered off again and dissolved in a mixture of 4-methyl-2-pentanone and a small amount of N,N-dimethylformamide. The solution is filtered till clear and the filtrate is concentrated to a volume of about 10 parts. The concentrate is triturated in methanol. The precipitated product is filtered off and dried, yielding 1.27 parts of 5-chloro-1-{3-[4-(5-chloro-1,3-dihydro-2-oxo-2H-benzimidazol-1-yl)-1-piperidinyl]propyl}-1,3-dihydro-2H-benzimidazol-2-one; mp. 229°-236° C.

EXAMPLE XXX

To a stirred solution of 1 part of 5-chloro-1-{1-[3-(1,3-dihydro-2-oxo-2H-benzimidazol-1-yl)propyl]-4-piperidinyl}-1,3-dihydro-2H-benzimidazol-2-one in 32 parts of ethanol is added a solution of 0.35 parts of (±)-2,3-dihydroxy-1,4-butanedioic acid in 8 parts of ethanol. Upon stirring, the product is allowed to crystallize. It is filtered off and dried, yielding 1 part of (±)-5-chloro-1-{1-[3-(1,3-dihydro-2-oxo-2H-benzimidazol-1-yl) propyl]-4-piperidinyl}-1,3-dihydro-2H-benzimidazol-2-one 2,3-dihydroxybutanedioate, ethanolate; mp. 153.5° C.

EXAMPLE XXXI

A solution of 7 parts of 5-chloro-1-[1-{3-[1,3-dihydro-3-(1-methylethenyl)-2-oxo-2H-benzimidazol-1-yl]-2-methylpropyl}-4-piperidinyl]-1,3-dihydro-2H-benzimidazol-2-one in 120 parts of ethanol is acidified with 2-propanol, previously saturated with gaseous hydrogen chloride. The whole is boiled for 5 minutes. The reaction mixture is evaporated and the residue is taken up in water. The mixture is alkalized with a concentrated ammonium hydroxide solution. The product is extracted with trichloromethane. The extract is dried, filtered and evaporated. The residue is crystallized from a mixture of 4-methyl-2-pentanone and ethanol. The product is filtered off and dried, yielding 1.3 parts (19.7%) of 5-chloro-1-{1-[3-(1,3-dihydro-2-oxo-2H-benzimidazol-1-yl)-2-methylpropyl]-4-piperidinyl}-1,3-dihydro-2H-benzimidazol-2-one; mp. 244° C.

EXAMPLE XXXII

A mixture of 2.3 parts of 1-(3-chloropropyl)-1,3-dihydro-2H-benzimidazol-2-one, 2.15 parts of 1,3-dihydro-1-(1,2,3,6-tetrahydro-4-pyridinyl)-2H-benzimidazol-2-one, 3.2 parts of sodium carbonate, 0.1 parts of potassium iodide and 80 parts of 4-methyl-2-pentanone is stirred and refluxed for 48 hours. After cooling to room temperature, water is added and the layers are separated. The organic phase is dried, filtered and evaporated. The residue is purified by column-chromatography over silica gel using a mixture of trichloromethane and 10% of methanol as eluent. The pure fractions are collected and the eluent is evaporated. The residue is crystallized from a mixture of N,N-dimethylformamide and water, yielding 2.5 parts (64.5%) of 1-{3-[3,6-dihydro-4-(1,3-dihydro-2-oxo-2H-benzimidazol-1-yl)-1-(2H)-pyridinyl]propyl}-1,3-dihydro-2H-benzimidazol-2-one; mp. 206.6° C.

EXAMPLE XXXIII

A stirred solution of 1 part of 5-chloro-1-{1-[3-(1,3-dihydro-2-oxo-2H-benzimidazol-1-yl)propyl]-4-piperidinyl}-1,3-dihydro-2H-benzimidazol-2-one in 20 parts of ethanol is saturated with gaseous hydrogen chloride. The formed hydrochloride salt is allowed to crystallize while stirring. It is filtered off and dried, yielding 0.6 parts (53%) of 5-chloro-1-{1-[3-(1,3-dihydro-2-oxo-2H-benzimidazol-1-yl)propyl]-4-piperidinyl}-1,3-dihydro-2H-benzimidazol-2-one hydrochloride hydrate; mp. 195.7° C.

EXAMPLE XXXIV

A solution of 1 part of 5-chloro-1-{1-[3-(1,3-dihydro-2-oxo-2H-benzimidazol-1-yl)propyl]-4-piperidinyl}-1,3-dihydro-2H-benzimidazol-2-one in 40 parts of ethanol is acidified with 2-propanol, previously saturated with gaseous hydrogen chloride. While cooling, the formed hydrochloride salt is allowed to crystallize, yielding 1 part (83%) of 5-chloro-1-{1-[3-(1,3-dihydro-2-oxo-2H-benzimidazol-1-yl)propyl]-4-piperidinyl}-1,3-dihydro-2H-benzimidazol-2-one hydrochloride, ethanolate; mp. 213.7° C.

EXAMPLE XXXV

A mixture of 6.7 parts of 5-chloro-1,3-dihydro-1-(3-hydroxypropyl)-2H-benzimidazol-2-one methanesulfonate, 4.2 parts of 4-(4-chlorophenyl)-4-piperidinol, 3.2 parts of sodium carbonate and 32 parts of 4-methyl-2-pentanone is stirred and heated at 50°-60° C. for 1.50 hours. The reaction mixture is poured onto ice-water. The precipitated product is filtered off and dissolved in trichloromethane. The solution is washed with water, dried, filtered and evaporated. The solid residue is purified by column-chromatography over silica gel using a mixture of trichloromethane and 10% of methanol as eluent. The pure fractions are collected and the eluent is evaporated. The solid residue is stirred in a small amount of trichloromethane. The product is filtered off and crystallized from 4-methyl-2-pentanone, yielding 2 parts (24%) of 5-chloro-1-{3-[4-(4-chlorophenyl)-4-hydroxy-1-piperidinyl]propyl}-1,3-dihydro-2H-benzimidazol-2-one; mp. 190.8° C.

EXAMPLE XXXVI

A mixture of 3.58 parts of 1-(3-chloropropyl)-1,3-dihydro-5,6-dimethyl-2H-benzimidazol-2-one, 3.17 parts of 4-(4-chlorophenyl)-4-piperidinol, 5.3 parts of sodium carbonate, 0.2 parts of potassium iodide and 160 parts of 4-methyl-2-pentanone is stirred and refluxed for 24 hours with water-separator. After cooling, water is added and the layers are separated. The organic phase is dried, filtered and evaporated. The residue is converted into the hydrochloride salt in methanol and 2-propanol. The salt is filtered off and dried, yielding 1.7 parts of 1-{3-[4-(4-chlorophenyl)-4-hydroxy-1-piperidinyl]propyl}-1,3-dihydro-5,6-dimethyl-2H-benzimidazol-2-one hydrochloride; mp. 260.8° C.

EXAMPLE XXXVII

A mixture of 5.6 parts of 6-chloro-1-(3-chloropropyl)-1,3-dihydro-2H-benzimidazol-2-one, 4.2 parts of 4-(4-chlorophenyl)-4-piperidinol, 6.4 parts of sodium carbonate, 0.2 parts of potassium iodide and 200 parts of 4-methyl-2-pentanone is stirred and refluxed overnight with water-separator. After cooling, water is added and the layers are separated. The 4-methyl-2-pentanone-phase is dried, filtered and evaporated. The oily residue is purified by column-chromatography over silica gel using a mixture of trichloromethane and 10% of methanol as eluent. The pure fractions are collected and the eluent is evaporated. The solid residue is crystallized from 4-methyl-2-pentanone, yielding 3.5 parts of 6-chloro-1-{3-[4-(4-chlorophenyl)-4-hydroxy-1-piperidinyl]propyl}-1,3-dihydro-2H-benzimidazol-2-one; mp. 180.6° C.

EXAMPLE XXXVIII

A mixture of 2.3 parts of 1-(3-chloropropyl)-1,3-dihydro-2H-benzimidazol-2-one, 2.12 parts of 4-(4-chlorophenyl)-4-piperidinol, 3.2 parts of sodium carbonate, 0.1 parts of potassium iodide and 80 parts of 4-methyl-2-pentanone is stirred and refluxed for 36 hours. After cooling to room temperature, water is added and the layers are separated. The organic phase is dried, filtered and evaporated. The residue is purified by column-chromatography over silica gel using a mixture of trichloromethane and 10% of methanol as eluent. The pure fractions are collected and the eluent is evaporated. The residue is crystallized from methylbenzene, yielding 1 part (26%) of 1-{3-[4-(4-chlorophenyl)-4-hydroxy-1-piperidinyl]propyl}-1,3-dihydro-2H-benzimidazol-2-one; mp. 134.2° C.

EXAMPLE XXXIX

A mixture of 5 parts of 1-(3-chloropropyl)-1,3-dihydro-3-(2-propenyl)-2H-benzimidazol-2-one, 3.17 parts of 4-(4-chlorophenyl)-4-piperidinol, 5.3 parts of sodium carbonate, 0.2 parts of potassium iodide and 200 parts of 4-methyl-2-pentanone is stirred and refluxed for 15 hours with water-separator. After cooling, water is added and the layers are separated. The organic phase is dried, filtered and evaporated. The residue is crystallized from 2-propanol, yielding, after drying, 3.5 parts (54.8%) of 1-{3-[4-(4-chlorophenyl) 4-hydroxy-1-piperidinyl]propyl}-1,3-dihydro-3-(2-propenyl)-2H-benzimidazol-2-one; mp. 141.3° C.

EXAMPLE XL

A mixture of 5 parts of 1-(3-chloropropyl)-1,3-dihydro-3-(1-methylethenyl)-2H-benzimidazol-2-one, 3.9 parts of 4-(4-fluorophenyl)-4-piperidinol, 5.3 parts of sodium carbonate and 80 parts of 4-methyl-2-pentanone is stirred and refluxed for 48 hours with water-separator. The reaction mixture is cooled to room temperature, water is added and the whole is alkalized with 15 parts of a sodium hydroxide solution 60%. The layers are separated and the organic phase is dried, filtered and evaporated. The residue is purified by column-chromatography over silica gel using a mixture of trichloromethane and 10% of methanol as eluent. The pure fractions are collected and the eluent is evaporated. The oily residue is dissolved in 2-propanone. The solution is acidified with 2-propanol, previously saturated with gaseous hydrogen chloride, and the whole is stirred and refluxed for 15 minutes. The solvent is evaporated and the formed hydrochloride salt is dissolved in water. The free base is liberated in the conventional manner with a diluted sodium hydroxide solution. The product is extracted with 4-methyl-2-pentanone. The extract is dried, filtered and evaporated. The residue is crystallized from methylbenzene. The product is filtered off and dried, yielding 2.5 parts of 1-{3-[4-(4-fluorophenyl)-4-hydroxy-1-piperidinyl]propyl}-1,3-dihydro-2H-benzimidazol-2-one; mp. 135.4° C.

EXAMPLE XLI

A mixture of 4.21 parts of 1-(3-chloropropyl)-1,3-dihydro-2H-benzimidazol-2-one, 5 parts of 4-[4-chloro-3-(trifluoromethyl)phenyl]-4-piperidinol, 5.3 parts of sodium carbonate, 0.1 parts of potassium iodide and 200 parts of 4-methyl-2-pentanone is stirred and refluxed for 6 hours with water-separator. The reaction mixture is cooled and water is added. The organic phase is separated, dried, filtered and evaporated. The residue is crystallized from 4-methyl-2-pentanone. The product is filtered off and dried, yielding 3.4 parts (41.6%) of 1-[3-{4-[4-chloro-3-(trifluoromethyl)phenyl]-4-hydroxy-1-piperidinyl}propyl]-1,3-dihydro-2H-benzimidazol-2-one; mp. 189.2° C.

EXAMPLE XLII

Following the procedure of Example XIII and using equivalent amounts of the appropriate starting materials, the following compunds are still obtained:
1-(4-chlorophenyl)-8-[3-(1,3-dihydro-2-oxo-2H-benzimidazol-1-yl)propyl)]-1,3,8-triazaspiro[4,5]decan-4one;
1-(4-chlorophenyl)-8-[3-(5-chloro-1,3-dihydro-2-oxo-2H-benzimidazol-1-yl)propyl]-1,3,8-triazspiro[4,5]decan-4-one;
8-[3-(1,3-dihydro-2-oxo-2H-benzimidazol-1-yl)-2-methylpropyl]-1-(4-fluorophenyl)-1,3,8-triazaspiro[4,5]decan-4-one;
8-[3-(1,3-dihydro-2-oxo-2H-benzimidazol-1-yl)-propyl]-1-(4-fluorophenyl)-3-methyl-1,3,8-triazaspiro[4,5]decan-4-one; and
8-[3-(1,3-dihydro-2-oxo-2H-benzimidazol-1-yl)propyl]-3-ethyl-1-(4-fluorophenyl)-1,3,8-triazaspiro[4,5]decan-4-one.

EXAMPLE XLIII

Following the procedure of Example XXIII and using equivalent amounts of the appropriate starting materials, the following compounds are still obtained:
5-chloro-1-{3-[4-(1,3-dihydro-5-methyl-2-oxo-2H-benzimidazol-1-yl)-1-piperidinyl]propyl}-1,3-dihydro-2H-benzimidazol-2-one;
5-(chloro-1-[3-{4-[1,3-dihydro-2-oxo-5-(trifluoromethyl)-2H-benzimidazol-1-yl]-1-piperidinyl}propyl]-1,3-dihydro-2H-benzimidazol-2-one;
1-{3-[4-(5,6-dichloro-1,3-dihydro-2-oxo-2H-benzimidazol-1-yl)-1-piperidinyl]propyl}-1,3-dihydro-2H-benzimidazol-2-one;
5-chloro-1-{3-[4-(5-chloro-1,3-dihydro-2-oxo-2H-benzimidazol-1-yl)-1-piperidinyl]-2-methylpropyl}-1,3-dihydro-2H-benzimidazol-2-one;
5-bromo-1-{3-[4-(5-chloro-1,3-dihydro-2-oxo-2H-benzimidazol-1-yl)-1-piperidinyl]propyl}-1,3-dihydro-2H-benzimidazol-2-one; and
1-{3-[4-(5-bromo-1,3-dihydro-2-oxo-2H-benzimidazol-1-yl)-1-piperidinyl]propyl}-1,3-dihydro-2H-benzimidazol-2-one.

EXAMPLE XLIV

Following the procedure of Example XXXVIII and using equivalent amounts of the appropriate starting materials, the following compounds are still obtained:
5-chloro-1-[3-{4-[4-chloro-3-(trifluoromethyl)phenyl]-4-hydroxy-1-piperidinyl}propyl]-1,3-dihydro-2H-benzimidazol-2-one;
5-chloro-1{3-[4-(4-chlorophenyl)-4-hydroxy-1-piperidinyl]-2-methylpropyl}-1,3-dihydro-2H-benzimidazol-2-one;
5-bromo-1-{3-[4-(4-chlorophenyl)-4-hydroxy-1-piperidinyl]propyl}-1,3-dihydro-2H-benzimidazol-2-one;
1-{3-[4-(4-bromophenyl)-4-hydroxy-1-piperidinyl]propyl}-1,3-dihydro-2H-benzimidazol-2-one;
1-{3-[4-(4-chlorophenyl)-4-hydroxy-1-piperidinyl]propyl}-1,3-dihydro-5-(trifluoromethyl)-2H-benzimidazol-2-one;
1-{3-[4-(4-chlorophenyl)-4-hydroxy-1-piperidinyl]propyl}-5,6-dichloro-1,3-dihydro-2H-benzimidazol-2-one; and
5-chloro-1-{3-[4-(4-chlorophenyl)-4-hydroxy-1-piperidinyl]propyl}-1,3-dihydro-3-(2-propenyl)-2H-benzimidazol-2-one.

EXAMPLE XLV

To a stirred and refluxing mixture of 35 parts of 4-fluoro-1,2-benzenediamine in 270 parts of dimethylbenzene is added dropwise, during a 2 hours-period, a solution of 57 parts of ethyl α-acetylbenzeneacetate in 90 parts of dimethylbenzene while meantime the formed water and the ethanol are distilled off (water-separator). The reaction mixture is evaporated and the residue is crystallized from 2-propanol. The product is filtered off and purified by column-chromatography over silica gel using a mixture of trichloromethane and methanol (98:2 by volume) as eluent. The pure fractions are collected and the eluent is evaporated, yielding 11 parts of 6-fluoro-1,3-dihydro-1-(1-methyl-2-phenylethenyl)-2H-benzimidazol-2-one; mp. 190° C.

To a stirred and hot (50° C.) mixture of 15 parts of 6-fluoro-1,3-dihydro-1-(1-methyl-2-phenylethenyl)-2H-benzimidazol-2-one, 3 parts of N,N,N-triethylbenzenemethanaminium chloride and 75 parts of a sodium hydroxide solution 60% are added dropwise 11.1 parts of 1-bromo-3-chloropropane (slightly exothermic reaction). Upon completion, stirring is continued for 4 hours at 60° C. The reaction mixture is cooled, water is added and the product is extracted with methylbenzene. The extract is dried, filtered and evaporated, yielding 20 parts (100%) of 1-(3-chloropropyl)-5-fluoro-1,3-dihydro-3-(1-methyl-2-phenylethenyl)-2H-benzimidazol-2-one as an oily residue.

EXAMPLE XLVI

A mixture of 30 parts of 1H-benzimidazol, 49 parts of 2-(4-chlorobutoxy)tetrahydro-2H-pyran, 21 parts of potassium hydroxide and 200 parts of ethanol is stirred and refluxed overnight. The reaction mixture is cooled to room temperature, filtered and the filtrate is evaporated. The residue is stirred in water and acidified with a diluted hydrochloric acid solution. The whole is stirred and heated for 30 minutes in a water-bath. After cooling to room temperature, the product is extracted with methylbenzene. The aqueous phase is separated and alkalized with ammonium hydroxide. The product is extracted with dichloromethane. The extract is dried, filtered and evaporated, yielding 50 parts of 1H-benzimidazole-1-butanol as an oily residue.

To a stirred mixture of 50 parts of 1H-benzimidazole-1-butanol and 375 parts of trichloromethane are added dropwise 35.2 parts of sulfinyl chloride. Upon completion, stirring is continued for 3 hours at reflux temperature. The reaction mixture is evaporated. The residue is taken up in trichloromethane. The whole is washed with ammonium hydroxide and the solvent is evaporated. The residue is purified by column-chromatography over silica gel using trichloromethane as eluent. The pure fractions are collected and the eluent is evaporated, yielding 22 parts (45%) of 1-(4-chlorobutyl)-1H-benzimidazole as an oily residue.

EXAMPLE XLVII

A mixture of 84 parts of ethyl 4[(4-chloro-2-nitrophenyl)amino]-1-piperidinecarboxylate and 750 parts of a hydrobromic acid solution 48% in water is stirred and refluxed for 4 hours. The precipitated product is filtered off, washed with water and petroleum-ether, and dried, yielding 71 parts (81%) of N-(4-chloro-2-nitrophenyl)-4-piperidinamine hydrobromide; mp. 275° C.

A mixture of 105 parts of 1-(3-chloropropyl)-1,3-dihydro-3-(1-methylethenyl)-2H-benzimidazol-2-one, 71 parts of N-(4-chloro-2-nitrophenyl)-4-piperidinamine hydrobromide, 53 parts of sodium carbonate, 0.2 parts of potassium iodide and 320 parts of 4-methyl-2-pentanone is stirred and refluxed for 24 hours with water-separator. The reaction mixture is cooled, water is added and the layers are separated. The organic phase is dried, filtered and evaporated, yielding 98.5 parts (100%) of 1-[3-{4-[(4-chloro-2-nitrophenyl)amino]-1-piperidinyl}propyl]-1,3-dihydro-3-(1-methylethenyl)-2H-benzimidazol-2-one as a residue.

A solution of 98.5 parts of 1-[3-{4-[(4-chloro-2-nitrophenyl)amino]-1-piperidinyl}propyl]-1,3-dihydro-3-(1-methylethenyl)-2H-benzimidazol-2-one in 360 parts of methylbenzene is acidified with 2-propanol, previously saturated with gaseous hydrogen chloride. After boiling for a while, an oil precipitates. The supernatent phase is decanted and the residual oil is suspended in water. The suspension is alkalized with a concentrated ammonium hydroxide solution. The product is extracted with methylbenzene. The extract is dried, filtered and evaporated. The residue is crystallized from 4-methyl-2-pentanone. The product is filtered off and dried, yielding 68 parts (75.5%) of 1-[3-{4-[(4-chloro-2-nitrophenyl)amino]-1-piperidinyl}propyl]-1,3-dihydro-2H-benzimidazol-2-one.

A mixture of 21.5 parts of 1-[3-{4-[(4-chloro-2-nitrophenyl)amino]-1-piperidinyl}propyl]-1,3-dihydro-2H-benzimidazol-2-one and 240 parts of methanol is hydrogenated at normal pressure and at room temperature with 5 parts of Raney-nickel catalyst. After the calculated amount of hydrogen is taken up, the catalyst is filtered off and the filtrate is evaporated, yielding 20 parts (100%) of 1-[3-{4-[(2-amino-4-chlorophenyl)amino]-1-piperidinyl}propyl]-1,3-dihydro-2H-benzimidazol-2-one as a residue.

EXAMPLE XLVIII

A mixture of 21.5 parts of 1-[3-{4-[(4-chloro-2-nitrophenyl)amino]-1-piperidinyl}propyl]-1,3-dihydro-2H-benzimidazol-2-one and 240 parts of methanol is hydrogenated at normal pressure and at room temperature with 10 parts of palladium-on-charcoal catalyst 10%. After the calculated amount of hydrogen is taken up, the catalyst is filtered off and the filtrate is evaporated, yielding 18.5 parts (100%) of 1-[3-{4-[(2-aminophenyl)amino]-1-piperidinyl}-propyl]-1,3-dihydro-2H-benzimidazol-2-one as a residue.

EXAMPLE IL

To a stirred mixture of 39.2 parts of 3-(2-nitrophenyl)amino-1-propanol and 225 parts of trichloromethane are added dropwise 35.7 parts of sulfinyl chloride (exothermic reaction: the temperature rises to 45° C.). Upon completion, stirring is continued for 6 hours at reflux temperature. The reaction mixture is evaporated, yielding 43 parts (100%) of N-(3-chloropropyl)-2-nitrobenzenamine as a residue.

A mixture of 43 parts of N-(3-chloropropyl)-2-nitrobenzenamine 47.8 parts of 5-chloro-1,3-dihydro-1-(4-piperidinyl)-2H-benzimidazol-2-one, 30.3 parts of N,N-diethylethanamine and 180 parts of N,N-dimethylacetamide is stirred and heated for 6 hours at 100° C. The reaction mixture is cooled and poured onto 1500 parts of water. The precipitated product is filtered off, washed with water and with 2,2'-oxybispropane and dried, yielding 64 parts (78.3%) of 5-chloro-1,3-dihydro-1-{1-[3-(2-nitrophenylamino)propyl]-4-piperidinyl}-2H-benzimidazol-2-one; mp. 220° C.

A mixture of 64 parts of 5-chloro-1,3-dihydro-1-{1-[3-(2-nitrophenylamino)propyl]-4-piperidinyl}-2H-benzimidazol-2-one in 200 parts of methanol and 225 parts of tetrahydrofuran is hydrogenated at normal pressure and at room temperature with 10 parts of Raney-nickel catalyst. After the calculated amount of hydrogen is taken up, the catalyst is filtered off over hyflo and the filtrate is evaporated. The residue is crystallized from a mixture of 2-propanol and ethanol. The product is filtered off and dried, yielding 42 parts (70.5%) of 1-[1-{3-[N-(2-aminophenyl)amino]propyl}-4-piperidinyl]-5-chloro-1,3-dihydro-2H-benzimidazol-2-one; mp. 196° C.

EXAMPLE L

A mixture of 4.21 parts of 1-(3-chloropropyl)-1,3-dihydro-2H-benzimidazol-2-one, 5 parts of 1-(4-chloro-3-methylphenyl)-1,3,8-triazaspiro[4,5]decan-4-one, 5.3 parts of sodium carbonate, 0.1 parts of potassium iodide and 200 parts of 4-methyl-2-pentanone is stirred and refluxed for 6 hours with water-separator. After cooling, water is added and the layers are separated. The organic phase is dried, filtered and evaporated. The residue is crystallized from a mixture of methanol and N,N-dimethylformamide. The product is filtered off and dried, yielding 3 parts (36.7%) of 1-(4-chloro-3-methylphenyl)-8-[3-(2,3-dihydro-2-oxo-1H-benzimidazol-1-yl)propyl]-1,3,8-triazaspiro[4,5]decan-4-one; mp. 208.6° C.

EXAMPLE LI

A mixture of 6 parts of 1-(3-chloropropyl)-1H-benzimidazole, 4.6 parts of 1-phenyl-1,3,8-triazaspiro[4,5]decan-4-one, 10 parts of sodium carbonate, 0.1 parts of potassium iodide and 80 parts of 4-methyl-2-pentanone is stirred and refluxed overnight. The reaction mixture is cooled, water is added and the layers are separated. The organic phase is dried, filtered and evaporated. The residue is purified by column-chromatography over silica gel using a mixture of trichloromethane and methanol (90:10 by volume) as eluent. The pure fractions are collected and the eluent is evaporated. The residue is crystallized from 4-methyl-2-pentanone, yielding 2 parts (25%) of 8-[3-(lH-benzimidazol-1-yl)propyl]-1-phenyl-1,3,8-triazaspiro[4,5]decan-4-one; mp. 191° C.

EXAMPLE LII

A mixture of 5.3 parts of 1-(3-chloropropyl)-1,3-dihydro-5-methyl-3-(1-methylethyl)-2H-benzimidazol-2-one, 4.3 parts of 1,3-dihydro-1-(4-piperidinyl)-2H-benzimidazol-2-one, 6.4 parts of sodium carbonate and 200 parts of 4-methyl-2-pentanone is stirred and refluxed overnight with water-separator. After cooling, water is added and the layers are separated. The 4-methyl-2-pentanone-phase is dried, filtered and evaporated. The oily residue is purified by column-chromatography over silica gel using a mixture of trichloromethane and methanol (90:10 by volume) as eluent. The pure fractions are collected and the eluent is evaporated, yielding 6 parts (67%) of 1-{3-[4-(2,3-dihydro-2-oxo-1H-benzimidazol-1-yl)-1-piperidinyl]propyl}-1,3-dihydro-5-methyl-3-(1-methylethyl)-2H-benzimidazol-2-one as an oily residue.

EXAMPLE LIII

Following the procedure of Example LII and using equivalent amounts of the appropriate starting materials, the following compounds are prepared:
1-{3-[4-(5-chloro-2,3-dihydro-2-oxo-1H-benzimidazol-1-yl)-1-piperidinyl]propyl}-1,3-dihydro-5-methyl-3-(1-methylethyl)-2H-benzimidazol-2-one as an oily residue; and
3-}3-[4-(5-chloro-2,3-dihydro-2-oxo-1H-benzimidazol-1-yl)-1-piperidinyl]propyl}-1,3-dihydro-5-methyl-1-(1-methylethyl)-2H-benzimidazol-2-one as an oily residue.

EXAMPLE LIV

A mixture of 14 parts of 1-(3-chloropropyl)-1,3-dihydro-3-(1-methylethyl)-2H-benzimidazol-2-one, 12.58 parts of 5-chloro-1,3-dihydro-1-(4-piperidinyl)-2H-benzimidazol-2-one, 5.3 parts of sodium carbonate, 0.1 parts of sodium iodide and 80 parts of 4-methyl-2-pentanone is stirred and refluxed for 24 hours. The reaction mixture is filtered and the filtrate is evaporated. The residue is taken up in 160 parts of 2-propanol and the whole is stirred and refluxed overnight with activated charcoal. The latter is filtered off over hyflo and the filtrate is allowed to cool. The precipitated product is filtered off, yielding a first crude fraction of 12.5 parts. The filtrate is treated with 2,2'-oxybispropane. The mixture is filtered and the filtrate is evaporated. The residue is triturated in 2-propanone. The product is filtered off, yielding a second crude fraction of 4.9 parts.

The combined crude crops (resp. 12.5 and 4.9 parts) are crystallized from methylbenzene. The product is filtered off and recrystallized from water, yielding 8.7 parts of 5-chloro-1-[1-{3-[2,3-dihydro-3-(1-methylethyl)-2-oxo-1H-benzimidazol-1-yl]propyl}-4-piperidinyl]-1,3-dihydro-2H-benzimidazol-2-one; mp. 165.2° C.

EXAMPLE LV

A mixture of 6 parts of 1-{3-[4-(2,3-dihydro-2-oxo-1H-benzimidazol-1-yl)-1-piperidinyl]propyl}-1,3-dihydro-5-methyl-3-(1-methylethyl)-2H-benzimidazol-2-one, 12 parts of a hydrochloric acid solution, 30 parts of water and 40 parts of ethanol is stirred first for a while at 50° C. and further for 1 hour at room temperature. The reaction mixture is evaporated and the residue is crystallized from a mixture of 4-methyl-2-pentanone and 2-propanol. The product is filtered off and dried, yielding 3.7 parts (40%) of 1-{3-[4-(2,3-dihydro-2-oxo-1H-benzimidazol-1-yl)-1-piperidinyl]propyl}-1,3-dihydro-5-methyl-2H-benzimidazol-2-one hydrochloride hydrate; mp. 251.4° C.

EXAMPLE LVI

Following the procedure of Example LV there is prepared 5-chloro-1-{1-[3-(2,3-dihydro-5-methyl-2-oxo-1H-benzimidazol-1-yl)propyl]-4-piperidinyl}-1,3-dihydro 2H-benzimidazol-2-one hydrochloride hydrate; mp. 213.3° C., starting from 1-{3-[4-(5-chloro-2,3-dihydro-2-oxo-1H-benzimidazol-1-yl)-1-piperidinyl]propyl}-1,3-dihydro-5-methyl-3-(1-methylethyl)-2H-benzimidazol-2-one.

EXAMPLE LVII

A mixture of 6.4 parts of 3-{3-[4-(5-chloro-2,3-dihydro-2-oxo-1H-benzimidazol-1-yl)-1-piperidinyl]propyl}-1,3-dihydro-5-methyl-1-(1-methylethyl)-2H-benzimidazol-2-one, 24 parts of a concentrated hydrochloric acid solution, 80 parts of ethanol and 50 parts of water is stirred for 1 hour at room temperature. The reaction mixture is evaporated and the residue is stirred in ammonium hydroxide. The product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is triturated in 4-methyl-2-pentanone. The product is filtered off and crystallized from a mixture of N,N-dimethylformamide and water, yielding 2.5 parts (40%) of 5-chloro-1-{1-[3-(2,3-dihydro-6-methyl-2-oxo-1H-benzimidazol-1-yl)propyl]-4-piperidinyl}-1,3-dihydro-2H-benzimidazol-2-one hemihydrate; mp. 195.4° C.

EXAMPLE LVIII

A mixture of 9 parts of 1-(3-chloropropyl)-1H-benzimidazole, 10 parts of 5-chloro-1,3-dihydro-1-(4-piperidinyl)-2H-benzimidazol-2-one, 7.4 parts of sodium carbonate and 200 parts of 4-methyl-2-pentanone is stirred and refluxed overnight. The reaction mixture is cooled, water is added and the layers are separated. The organic phase is dried, filtered and evaporated. The residue is crystallized from 4-methyl-2-pentanone, yielding 2.9 parts (14%) of 1-{1-[3-(1H-benzimidazol-1-yl)propyl]-4-piperidinyl}-5-chloro-1,3-dihydro-2H-benzimidazol-2-one; mp. 224° C.

EXAMPLE LIX

A mixture of 6.7 parts of 1-(4-chlorobutyl)-1H-benzimidazole, 5.5 parts of 1,3-dihydro-1-(4-piperidinyl)-2H-benzimidazol-2-one, 5.3 parts of sodium carbonate, 0.1 parts of potassium iodide and 200 parts of 4-methyl-2-pentanone is stirred and refluxed overnight. The reaction mixture is cooled, water is added and the layers are separated. The organic phase is dried, filtered and evaporated. The residue is purified twice by column-chromatography over silica gel using first a mixture of trichloromethane and methanol (95:5 by volume) and then a mixture of trichloromethane and methanol (90:10 by volume) as eluent. The pure fractions are collected and the eluent is evaporated. The residue is crystallized from 4-methyl-2-pentanone. The product is filtered off and dried, yielding 1.8 parts of 1-{1-[4-(1H-benzimidazol-1-yl)butyl]-4-piperidinyl}-1,3-dihydro-2H-benzimidazol-2-one; mp. 157.1° C.

EXAMPLE LX

A mixture of 4.7 parts of 3-(3-chloropropyl)-2(3H)-benzoxazolone, 5 parts of 5-chloro-1,3-dihydro-1-(4-piperidinyl)-2H-benzimidazol-2-one, 6.4 parts of sodium carbonate and 200 parts of 4-methyl-2-pentanone is stirred and refluxed overnight with water-separator. After cooling, water is added and the layers are separated. The 4-methyl-2-pentanone phase is dried, filtered and evaporated. The residue is boiled in a mixture of 4-methyl-2-pentanone, 2-propanol and methanol. The whole is cooled and the product is filtered off and dried, yielding 4 parts (47%) of 5-chloro-1-{1-[3-(2-oxo-3(2H)-benzoxazolyl)propyl]-4-piperidinyl}-1,3-dihydro-2H-benzimidazol-2-one; mp. 212.3° C.

EXAMPLE LXI

A mixture of 5.4 parts of 3-(3-bromopropyl)-2(3H)-benzothiazolone, 4.5 parts of 5-chloro-1,3-dihydro-1-(4-piperidinyl)-2H-benzimidazol-2-one, 5.3 parts of sodium carbonate, 0.1 parts of potassium iodide and 200 parts of 4-methyl-2-pentanone is stirred and refluxed for 3 hours with water-separator. After cooling, water is added and the layers are separated. The organic phase is dried, filtered and evaporated. The residue is crystallized from a mixture of 4-methyl-2-pentanone and 2-propanone. The product is filtered off and dried, yielding 2.5 parts (31%) of 5-chloro-1,3-dihydro-1-{1-[3-(2-oxo-3(2H)-benzothiazolyl)propyl]-4-piperidinyl}-2H-benzimidazol-2-one; mp. 184.1° C.

EXAMPLE LXII

A mixture of 5 parts of 5-chloro-1,3-dihydro-1-(4-piperidinyl)-2H-benzimidazol-2-one, 3.7 parts of sodium carbonate and 200 parts of 4-methyl-2-pentanone is stirred and refluxed with water-separator. Then there are added 4.8 parts of 1-(3-bromopropyl)-1H-benzotriazole and stirring is continued overnight at reflux temperature. The reaction mixture is cooled, water is added and the undissolved product is filtered off and set aside. The organic phase is separated from the filtrate, dried, filtered and evaporated. The residue is combined with the undissolved product (see above) and purified by column-chromatography over silica gel using a mixture of trichloromethane and methanol (95:5 by volume) as eluent. The pure fractions are collected and the eluent is evaporated. The residue is crystallized from 4-methyl-2-pentanone, yielding 2 parts (25%) of 1-{1-[3-(1H-benzotriazol-1-yl)propyl]-4-piperidinyl}-5-chloro-1,3-dihydro-2H-benzimidazol-2-one; mp. 203.4° C.

EXAMPLE LXIII

A mixture of 38 parts of carbon disulfide, 6 parts of 1-[1-{3-[N-(2-aminophenyl)amino]propyl}-4-piperidinyl]-5-chloro-1,3-dihydro-2H-benzimidazol-2-one and 32 parts of ethanol is stirred and refluxed for 24 hours. The reaction mixture is evaporated and the residue is crystallized from ethanol. The product is filtered off and recrystallized from a mixture of N,N-dimethylformamide and water, yielding 3 parts (45.5%) of 5-chloro-1-{1-[3-(2,3-dihydro-2-thioxo-1H-benzimidazol-1-yl)-propyl]-4-piperidinyl}-1,3-dihydro-2H-benzimidazol-2-one; mp. 266.6° C.

EXAMPLE LXIV

A mixture of 4 parts of 1-[1-{3-[N-(2-amino-5-chlorophenyl)amino]propyl}-4-piperidinyl]-1,3-dihydro-2H-benzimidazol-2-one, 6 parts of a concentrated hydrochloric acid solution and 30 parts of formic acid is stirred and refluxed overnight. The reaction mixture is evaporated and water is added to the residue. The whole is alkalized with a diluted ammonium hydroxide solution and the product is extracted with trichloromethane. The extract is dried, filtered and evaporated. The residue is crystallized from 4-methyl-2-pentanone. The product is filtered off and recrystallized from 2-propanol, yielding 1.1 parts (27%) of 1-{1-[3-(6-chloro-1H-benzimidazol-1-yl)propyl]-4-piperidinyl}-1,3-dihydro-2H-benzimidazol-2-one; mp. 214.9° C.

EXAMPLE LXV

A mixture of 18.3 parts of 1-[3-{4-[(2-aminophenyl)amino]-1-piperidinyl}propyl]-1,3-dihydro-2H-benzimidazol-2-one, 65 parts of carbon disulfide and 60 parts of ethanol is stirred and refluxed for 24 hours. The reaction mixture is evaporated. The residue is crystallized from ethanol. The product is filtered off and dried, yielding 4.5 parts (19.7%) of 1-{3-[4-(2,3-dihydro-2-thioxo-1H-benzimidazol-1-yl)-1-piperidinyl]propyl}-1,3-dihydro-2H-benzimidazol-2-one; mp. 248.5° C.

EXAMPLE LXVI

A mixture of 20 parts of 1-[3-{4-[(2-amino-4-chlorophenyl)amino]-1-piperidinyl}propyl]-1,3-dihydro-2H-benzimidazol-2-one, 52 parts of carbon disulfide and 120 parts of ethanol is stirred and refluxed for 24 hours. The reaction mixture is filtered after cooling, and the filtrate is evaporated. The residue is crystallized from 2-propanol. The product is filtered off and recrystallized from ethanol, yielding, after drying, 7.5 parts (34%) of 1-{3-[4-(5-chloro-2,3-dihydro-2-thioxo-1H-benzimidazol-1-yl)-1-piperidinyl]propyl}-1,3-dihydro-2H-benzimidazol-2-one; mp. 254.3° C.

EXAMPLE LXVII

A mixture of 4.94 parts of 1-(4-chlorobutyl)-1,3-dihydro-2H-benzimidazol-2-one, 4.23 parts of 4-(4-chlorophenyl)-4-piperidinol, 5.3 parts of sodium carbonate, 0.1 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated. The residue is crystallized from 4-methyl-2-pentanone. The product is filtered off and dried, yielding 4 parts of 1-{4-[4-(4-chlorophenyl)-4-hydroxy-1-piperidinyl]butyl}-1,3-dihydro-2H-benzimidazol-2-one; mp. 160.6° C.

EXAMPLE LXVIII

A mixture of 4.86 parts of 1-(3-chloropropyl)-1H-benzimidazole, 4.24 parts of 4-(4-chlorophenyl)-4-piperidinol, 5.3 parts of sodium carbonate, 0.1 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated. The residue is crystallized from 4-methyl-2-pentanone. The product is filtered off and dried, yielding 5 parts (67.6%) of 1-[3-(1H-benzimidazol-1-yl)propyl]-4-(4-chlorophenyl)-4-piperidinol; mp. 160° C.

EXAMPLE LXIX

A mixture of 7 parts of 1-(3-chloropropyl)-5-fluoro-1,3-dihydro-3-(1-methyl)-2-phenylethenyl)-2H-benzimidazol-2-one, 5 parts of 5-chloro-1,3-dihydro-1-(4-piperidinyl)-2H-benzimidazol-2-one, 4.25 parts of sodium carbonate, 0.1 parts of potassium iodide and 200 parts of 4-methyl-2-pentanone is stirred and refluxed overnight. The mixture is cooled to room temperature, water is added and the layers are separated. The organic phase is dried, filtered and evaporated. The residue is stirred and refluxed overnight with a solution of 55 parts of a hydrochloric acid solution 6N in 40 parts of ethanol. The solvent is evaporated and the residue is taken up in water. The whole is alkalized with ammonium hydroxide and the product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is converted into the hydrochloride salt in 2-propanol. The salt is filtered off and dried, yielding 1.2 parts of 1-{3-[4-(5-chloro-2,3-dihydro-2-oxo-1H-benzimidazol-1-yl)-1-piperidinyl]propyl}-5-fluoro-1,3-dihydro-2H-benzimidazol-2-one hydrochloride.hydrate; mp. 250° C.

EXAMPLE LXX 10.2 Parts of 5-chloro-1-{1-[3-(2,3-dihydro-2-oxo-1H-benzimidazol-1-yl)propyl]-4-piperidinyl}-1,3-dihydro-2H-benzimidazol-2-one are converted into the (+)-2,3-dihydroxybutanedioate salt in 100 parts of water at reflux temperature. The solution is treated for 10 minutes with a mixture of 0.5 parts of activated charcoal and 0.2 parts of hyflo. The latter is filtered off over hyflo and the filtrate is cooled till an oily precipitate is formed. The oily product solidifies upon heating for a while. The whole is allowed to cool to room temperature and stirred for 3 hours at this temperature. The product is filtered off, washed with water and dried in vacuo for 18 hours at 60° C., yielding 10.24 parts (85.3%) of 5-chloro-1-{1-[3-(2,3-dihydro-2-oxo-1H-benzimidazol-1-yl)propyl]-4-piperidinyl}-1,3-dihydro-2H-benzimidazol-2-one hemi-[R-(R',R')](+)-2,3-dihydroxybutanedioate hydrate; mp. 184.1° C.; $[\alpha] = +5.13°$ (c = 1% $CH_3OH$).

EXAMPLE LXXI

A mixture of 9.25 parts of 1-(4-chlorobutyl)-1,3-dihydro-3-(1-methylethenyl)-2H-benzimidazol-2-one, 7.55 parts of 5-chloro-1,3-dihydro-1-(4-piperidinyl)-2H-benzimidazol-2-one, 10.6 parts of sodium carbonate, 0.1 parts of potassium iodide and 200 parts of 4-methyl-2-pentanone is stirred and refluxed for 18 hours. After cooling, water is added and the layers are separated. The organic phase is dried, filtered and evaporated. The residue is dissolved in 40 parts of ethanol and the solution is acidified with 30 parts of a concentrated hydrochloric acid solution. The whole is stirred for 30 minutes and the solvent is evaporated. The residue is suspended in water and the suspension is alkalized with ammonium hydroxide. The product is extracted with trichloromethane. The extract is dried, filtered and evaporated. The residue is purified by column-chromatography over silica gel using a mixture of trichloromethane and methanol (90:10 by volume) as eluent. The pure fractions are collected and the eluent is evaporated. The residue is crystallized from a mixture of N,N-dimethylformamide and water. The product is filtered off and dried, yielding 6.5 parts (46%) of 5-chloro-1-{1-[4-(2,3-dihydro-2-oxo-1H-benzimidazol-1-yl)butyl]-4-piperidinyl}-1,3-dihydro-2H-benzimidazol-2-one hemihydrate; mp. 258° C.

EXAMPLE LXXII

A mixture of 4.15 parts of 1-(3-chloropropyl)-1,3-dihydro-3-(1-methylethenyl)-2H-benzimidazol-2-one, 3.9 parts of 1-(1-methylethyl)-3-(4-piperidinyl)-2H-benzimidazol-2-one, 3.2 parts of sodium carbonate, 0.1 parts of potassium iodide and 120 parts of 4-methyl-2-pentanone is stirred and refluxed overnight. The reaction mixture is cooled to room temperature, water is added and the layers are separated. The organic phase is dried, filtered and evaporated. The residue is stirred for 30 minutes with a solution of 12 parts of a concentrated hydrochloric acid solution in 40 parts of ethanol. The solvent is evaporated and the residue is suspended in water. The suspension is alkalized with a diluted ammonium hydroxide solution and the product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 4-methyl-2-pentanone. The product is filtered off and dried, yielding 4.2 parts (64%) of 1-{1-[3-(2,3-dihydro-2-oxo-1H-benzimidazol-1-yl)propyl]-4-piperidinyl}-1,3-dihydro-3-(1-methylethyl)-2H-benzimidazol-2-one; mp. 174.3° C.

EXAMPLE LXXIII

A mixture of 2.21 parts of 1-{3-[4-(5-chloro-2,3-dihydro-2-thioxo-1H-benzimidazol-1-yl)-1-piperidinyl]propyl}-1,3-dihydro-2H-benzimidazol-2-one, 0.71 parts of iodomethane, 0.28 parts of sodium methanolate and 40 parts of methanol is stirred overnight at room temperature. The reaction mixture is evaporated. The residue is stirred with water and the product is extracted with trichloromethane. The extract is dried, filtered and evaporated. The residue is crystallized from 4-methyl-2-pentanone. The product is filtered off and dried, yielding 1.1 parts of 1-[3-{4-[5-chloro-2-(methylthio)-1H-benzimidazol-1-yl]-1-piperidinyl}propyl]-1,3-dihydro-2H-benzimidazol-2-one; mp. 196.1° C.

EXAMPLE LXXIV

A mixture of 5 parts of 5-chloro-1-{1-[3-(2,3-dihydro-2-oxo-1H-benzimidazol-1-yl)propyl]-4-piperidinyl}-1,3-dihydro-2H-benzimidazol-2-one, 10 parts of acetic acid anhydride and 90 parts of methylbenzene is stirred and refluxed overnight. The reaction mixture is cooled, water is added and the whole is alkalized with a diluted sodium carbonate solution. The layers are separated and the organic phase is dried, filtered and evaporated. The residue is crystallized from methylbenzene. The product is filtered off and recrystallized from methylbenzene, yielding 4.5 parts of 3-acetyl-5-chloro-1-{1-[3-(3-acetyl-2,3-dihydro-2-oxo-1H-benzimidazol-1-yl)propyl]-4-piperidinyl}-1,3-dihydro-2H-benzimidazol-2-one; mp. 185.3° C.

We claim:

1. A chemical compound selected from the group consisting of a 1-(benzatriazolylalkyl)piperidine derivative having the formula:

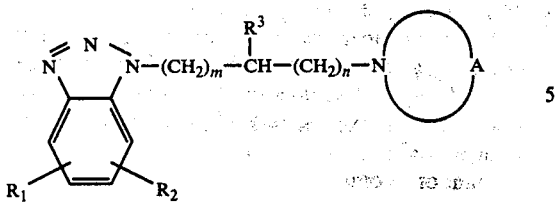

and the pharmaceutically acceptable acid addition salts thereof, wherein:

$R^1$ and $R^2$ are each independently selected from the group consisting of hydrogen, halo, lower alkyl and trifluoromethyl;

$R^3$ is a member selected from the group consisting of hydrogen and methyl;

m and n are each an integer of from 1 to 2 inclusive; and the radical

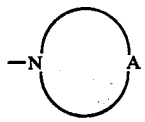

is a member selected from the group consisting of:
a. a radical having the formula:

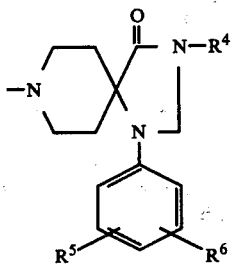

wherein $R^4$ is a member selected from the group consisting of hydrogen and lower alkyl; and $R^5$ and $R^6$ are each independently selected from the group consisting of hydrogen, halo, lower alkyl and trifluoromethyl;

b. a radical having the formula:

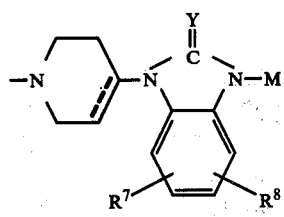

wherein $R^7$ and $R^8$ are each independently selected from the group consisting of hydrogen, halo, lower alkyl and trifluoromethyl; Y is a member selected from the group consisting of O and S; M is a member selected from the group consisting of hydrogen, lower alkyl and lower alkylcarbonyl; and the dotted line indicates that the double bond between the 3 and 4 carbon atoms of the piperidine nucleus is optional, provided that when said Y is S, then there is a single bond between said 3 and 4 carbon atoms of the piperidine nucleus, and then said M is hydrogen;

c. a radical having the formula:

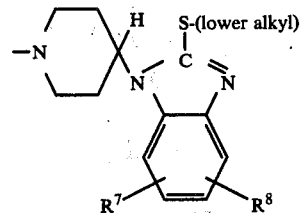

wherein $R^7$ and $R^8$ are each independently selected from the group consisting of hydrogen, halo, lower alkyl, and trifluoromethyl; and d. a radical having the formula:

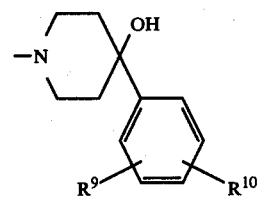

wherein $R^9$ is selected from the group consisting of hydrogen, halo, lower alkyl and trifluoromethyl, and $R^{10}$ is selected from the group consisting of hydrogen and halo.

2. A chemical compound selected from the group consisting of 1- 1-[3-(1H-benzotriazol-1-yl)propyl]-4-piperidinyl- consisting of 1 - 1-[3-(1H-benzotriazol-1-yl)propyl]-4-piperidinyl-5-chloro-1,3-dihydro-2H-benzimidazol-2-one and the pharmaceutically acceptable acid addition salts thereof.

3. A pharmaceutical composition comprising a pharmaceutically acceptable inert carrier material and as an active ingredient an effective antiemetic amount of a chemical compound selected from the group consisting of a 1-(benzotriazolylalkyl)piperidine derivative having the formula:

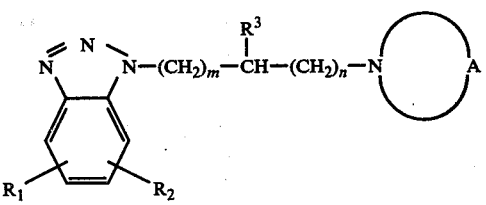

and the pharmaceutically acceptable acid addition salts thereof, wherein:

$R^1$ and $R^2$ are each independently selected from the group consisting of hydrogen, halo, lower alkyl and trifluoromethyl;

$R^3$ is a member selected from the group consisting of hydrogen and methyl;

m and n are each an integer of from 1 to 2 inclusive; and the radical

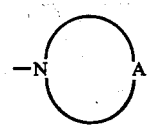

is a member selected from the group consisting of:
a. a radical having the formula:

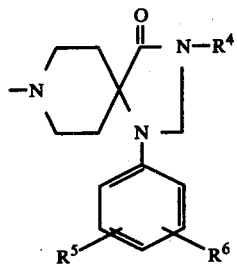

wherein R⁴ is a member selected from the group consisting of hydrogen and lower alkyl; and R⁵ and R⁶ are each independently selected from the group consisting of hydrogen, halo, lower alkyl and trifluoromethyl;
b. a radical having the formula:

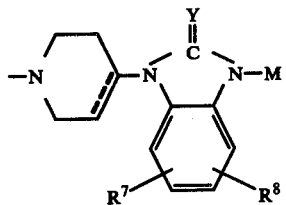

wherein R⁷ and R⁸ are each independently selected from the group consisting of hydrogen, halo, lower alkyl and trifluoromethyl; Y is a member selected from the group consisting of O and S; M is a member selected from the group consisting of hydrogen lower alkyl and lower alkylcarbonyl; and the dotted line indicates that the double bond between the 3 and 4 carbon atoms of the piperidine nucleus is optional, provided that when said Y is S, then there is a single bond between said 3 and 4 carbon atoms of the piperidine nucleus, and the said M is hydrogen;
c. a radical having the formula:

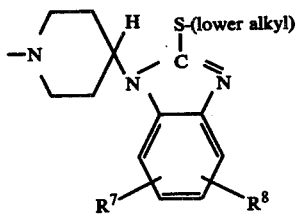

wherein R⁷ and R⁸ are each independently selected from the group consisting of hydrogen, halo, lower alkyl, and trifluoromethyl; and
d. a radical having the formula:

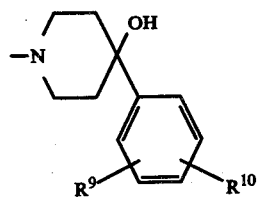

wherein R⁹ is selected from the group consisting of hydrogen, halo, lower alkyl and trifluoromethyl, and R¹⁰ is selected from the group consisting of hydrogen and halo.

4. A pharmaceutical composition in dosage unit form comprising per dosage unit an effective antiemetic amount of a compound selected from the group consisting of a 1-(benzotriazolylalkyl)piperidine derivative having the formula:

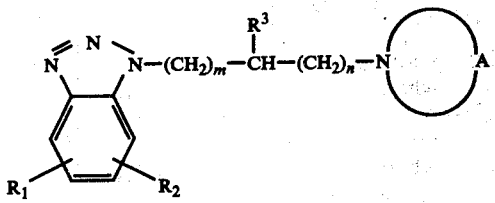

and the pharmaceutically acceptable acid addition salts thereof, wherein:
R¹ and R² are each independently selected from the group consisting of hydrogen, halo, lower alkyl and trifluoromethyl;
R³ is a member selected from the group consisting of hydrogen and methyl;
m and n are each an integer of from 1 to 2 inclusive; and the radical

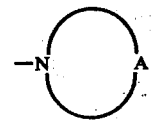

is a member selected from the group consisting of:
a. a radical having the formula:

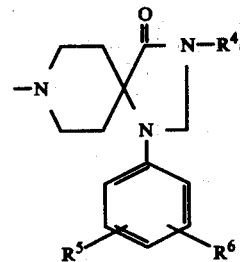

wherein R⁴ is a member selected from the group consisting of hydrogen and lower alkyl; and R⁵ and R⁶ are each independently selected from the group consisting of hydrogen, halo, lower alkyl and trifluoromethyl;
b. a radical having the formula:

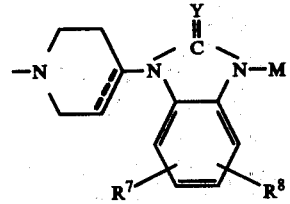

wherein R⁷ and R⁸ are each independently selected from the group consisting of hydrogen, halo, lower alkyl and trifluoromethyl; Y is a member selected from the group consisting of O and S; M is a member selected from the group consisting of hydrogen, lower alkyl and lower alkylcarbonyl; and the dotted line indicates that the double bond between the 3 and 4 carbon atoms of the piperidine nucleus is optional, provided that when said Y is S, then there is a single bond between said 3 and 4 carbon atoms of the piperidine nucleus, and then said M is hydrogen;

c. a radical having the formula:

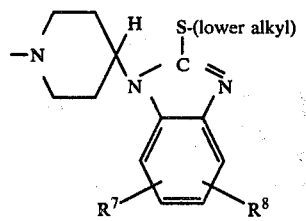

wherein $R^7$ and $R^8$ are each independently selected from the group consisting of hydrogen, halo, lower alkyl, and trifluoromethyl; and d. a radical having the formula:

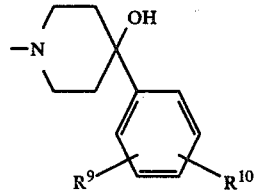

wherein $R^9$ is selected from the group consisting of hydrogen, halo, lower alkyl and trifluoromethyl, and $R^{10}$ is selected from the group consisting of hydrogen and halo;

is admixture with a pharmaceutical carrier.

5. The pharmaceutical composition of claim 4 wherein said pharmaceutical carrier is a solid, ingestible carrier.

6. The pharmaceutical composition of claim 4 wherein said pharmaceutical carrier is a liquid, ingestible carrier.

7. The pharmaceutical composition of claim 4 wherein said pharmaceutical carrier is a sterile liquid suitable for parenteral use.

8. A pharmaceutical composition in dosage unit form comprising per dosage unit an effective antiemetic amount of a compound selected from the group consisting of 1-1-[3-(1H-benzotriazol-1-yl)propyl]-4-piperidinyl-5-chloro-1,3-dihydro-2H-benzimidazol-2-one and the pharmaceutically acceptable acid addition salts thereof in admixture with a pharmaceutically acceptable carrier.

9. A method of inhibiting emesis which comprises the systemic administration in warm-blooded animals in need of such treatment of an effective antiemetic amount of a compound selected from the group consisting of a 1-(benzotriazolylalkyl)piperidine derivative having the formula:

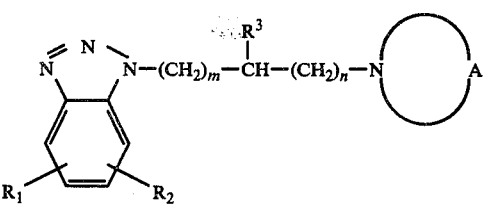

and the pharmaceutically acceptable acid addition salts thereof, wherein:

$R^1$ and $R^2$ are each independently selected from the group consisting of hydrogen, halo, lower alkyl and trifluoromethyl;

$R^3$ is a member selected from the group consisting of hydrogen and methyl;

m and n are each an integer of from 1 to 2 inclusive;

and the radical

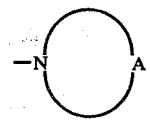

is a member selected from the group consisting of:

a. a radical having the formula:

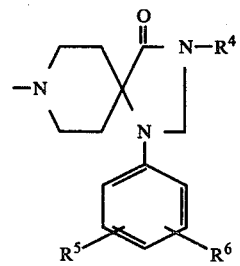

wherein $R^4$ is a member selected from the group consisting of hydrogen and lower alkyl; and $R^5$ and $R^6$ are each independently selected from the group consisting of hydrogen, halo, lower alkyl and trifluoromethyl;

b. a radical having the formula:

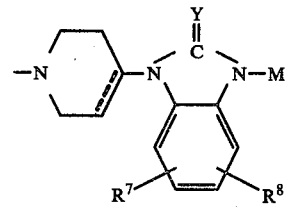

wherein $R^7$ and $R^8$ are each independently selected from the group consisting of hydrogen, halo, lower alkyl and trifluoromethyl; Y is a member selected from the group consisting of O and S; M is a member selected from the group consisting of hydrogen, lower alkyl and lower alkylcarbonyl; and the dotted line indicates that the double bond between the 3 and 4 carbon atoms of the piperidine nucleus is optional, provided that when said Y is S, then there is a single bond between said 3 and 4 carbon atoms of the piperidine nucleus, and then said M is hydrogen;

c. a radical having the formula:

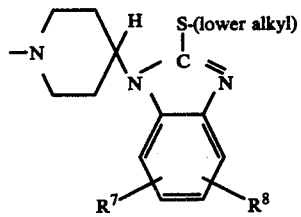

wherein $R^7$ and $R^8$ are each independently selected from the group consisting of hydrogen, halo, lower alkyl, and trifluoromethyl; and d. a radical having the formula:

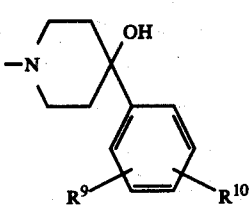

wherein $R^9$ is selected from the group consisting of hydrogen, halo, lower alkyl and trifluoromethyl, and $R^{10}$ is selected from the group consisting of hydrogen and halo; in admixture with a pharmaceutical carrier.

10. A method of inhibiting emesis which comprises the systemic administration is warm-blooded animals in need of such treatment of an effective antiemetic amount of a compound selected from the group consisting of 1-1-[3-(1H-benzotriazol-1-yl)propyl]-4-piperidinyl-5-chloro-1,3-dihydro-2H-benzimidazol-2-one and the pharmaceutically acceptable acid addition salts thereof in admixture with a pharmaceutical carrier.

* * * * *